United States Patent [19]

Cardarelli

[11] 4,400,374
[45] * Aug. 23, 1983

[54] CONTROLLED RELEASE OF COMPOUNDS UTILIZING A PLASTIC MATRIX

[75] Inventor: Nathan F. Cardarelli, Barberton, Ohio

[73] Assignee: Environmental Chemicals, Inc., Wauconda, Ill.

[*] Notice: The portion of the term of this patent subsequent to Aug. 28, 1996 has been disclaimed.

[21] Appl. No.: 171,835

[22] Filed: Jul. 24, 1980

Related U.S. Application Data

[63] Continuation-in-part of Ser. No. 51,102, Jun. 22, 1979, Pat. No. 4,299,613, which is a continuation-in-part of Ser. No. 14,118, Feb. 20, 1979, Pat. No. 4,228,614, which is a continuation-in-part of Ser. No. 5,174, Jan. 22, 1979, Pat. No. 4,237,114, which is a continuation-in-part of Ser. No. 916,570, Jun. 19, 1978, Pat. No. 4,166,111.

[51] Int. Cl.³ ............................................. A01N 55/04
[52] U.S. Cl. ..................................... 424/78; 424/81
[58] Field of Search ................................ 424/78, 81

[56] References Cited

U.S. PATENT DOCUMENTS

| | | | |
|---|---|---|---|
| 2,109,642 | 3/1938 | Hunt | 43/124 |
| 3,236,793 | 2/1966 | Robins et al. | 424/288 X |
| 3,417,181 | 12/1968 | Cardarelli | 424/229 |
| 3,590,119 | 6/1971 | Cardarelli et al. | 424/22 |
| 4,010,141 | 3/1977 | Onozuka et al. | 424/78 X |
| 4,012,221 | 3/1977 | Walker et al. | 424/83 X |
| 4,012,347 | 3/1977 | Gitlitz et al. | 424/76 X |
| 4,166,111 | 8/1979 | Cardarelli | 424/78 |
| 4,228,614 | 10/1982 | Cardarelli | 43/131 |
| 4,237,113 | 12/1980 | Cardarelli | 424/78 |
| 4,237,114 | 12/1982 | Cardarelli | 424/78 |

Primary Examiner—Leonard Schenkman
Attorney, Agent, or Firm—Lee, Smith & Jager

[57] ABSTRACT

A composition and method for the controlled release of compounds from a plastic dispenser, usually a thermoplastic, generally in association with a porosigen in contact with water, for example, an aquatic environment or soil moisture. Thermoplastic dispensers are generally made from a water insoluble polymer such as polyethylene, polypropylene, ethylene vinyl acetate, polyamide, polystyrene, polyvinyl acetate, polyurethane, etc. Thermoset plastics, such as epoxy, are also used. The porosigen, depending upon the desired end use and release rate of a compound, can have a solubility of less than 0.1 or 0.001 grams per 100 grams of water, or up to 100 grams per 100 grams of water. The released compound, for example, a larvicide, a molluscicide, a nematicide, a trace nutrient, a plant regulant, etc., is contained in the thermoplastic dispenser. The combination of the plastic dispenser containing the porosigen and compound results in a slow release which can last for days, months, and even years, through dissolution of the porosigen and the formation of a porous network permitting water to contact the dispersed compound located in the interior portions of the dispenser.

51 Claims, 3 Drawing Figures

CONTROLLED RELEASE OF COMPOUNDS UTILIZING A PLASTIC MATRIX

CROSS-REFERENCE

This application is a continuation-in-part of two of my copending applications, to-wit: "CONTROLLED RELEASE OF TRACE NUTRIENTS," filed June 22, 1979, bearing U.S. Ser. No. 51,102 (now U.S. Pat. No. 4,299,613); and "FLOATING CHIP DISPENSER," filed Feb. 20, 1979, bearing U.S. Ser. No. 14,118 (now U.S. Pat. No. 4,228,613). Application Ser. No. 51,102 is a continuation-in-part of application Ser. No. 14,118; which in turn is a continuation-in-part of my earlier copending application entitled "A METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC DISEPENSER" filed Jan. 22, 1979 as U.S. Ser. No. 5,174 (now U.S. Pat. No. 4,237,114); which application Ser. No. 5,174 in turn is a continuation-in-part of an application bearing the immediately above title filed on June 19, 1978, as U.S. Ser. No. 916,570 (now U.S. Pat. No. 4,166,111). A related application is entitled "CONTROLLED RELEASE OF HERBICIDE COMPOUNDS UTILIZING A PLASTIC MATRIX," filed on July 24, 1980, bearing U.S. Ser. No. 171,834, currently pending.

BACKGROUND ART

The present invention relates to the controlled release of compounds utilizing a plastic dispenser with a porosigen contained therein.

More specifically, the invention relates to the controlled release of organotins and other compounds utilized as a molluscicide, the controlled release of, larvicides, as well as the controlled release of trace nutrients, nematicides, soil insecticides, etc., from a plastic dispenser.

It is well known that biocidal materials can be incorporated into an elastomer matrix and caused to release at a rate efficacious with pest destruction. U.S. Pat. No. 3,417,181 teaches that organotin toxicants can be dissolved in an elastomer-type matrix and caused to release through a diffusion-dissolution mechanism when exposed to water. The crux of this semial invention was keyed to the necessity of the agent being soluble in the polymer. Similarly, U.S. Pat. Nos. 3,590,119; 3,426,473; 3,851,053; and 3,639,583 extend the scope of the art to embrace new formulations encompassing different elastomers, specific release regulants that affect the diffusion path length, and the like, but again the key concept is the necessity of agent solubility in the elastomer. Agents incorporated are organic pesticides, and the generic matrix type is elastomers such as natural rubber, styrene-butastyrene rubber, and the like. In contrast, U.S. Pat. No. 4,012,221 teaches that inorganic copper salts capable of being released into water are incorporated in a moderately crosslinked elastomer in which the copper salts are insoluble.

It is well known to the compounding art that agents not soluble within a polymeric matrix wil not move at an efficacious rate through said matrix to said matrix surface and thus enter the ambient environment.

Almost all organic pesticidal agents lack solubility in plastic matrices such as thermoplastic or thermoset. Similarly, inorganic pesticidal agents are likewise insoluble in known thermoplastic or thermosetting polymers. Similarly, inorganic chemicals utilized as trace nutrients in agriculture are insoluble in plastic materials.

One method of causing an insoluble organic agent to emit from a plastic dispensing unit is to use a third phase material that is (1) soluble in some extent in said plastic, and (2) will carry said organic agent in solutions or serve as a migratory pathway for said agent to reach the surface of said dispenser. It is, of course, recognized that the incorporated agent must reach the plastic/external environment interface to have any effect on organisms inhibiting the external environment. U.S. Pat. Nos. 2,956,073 and 3,116,201 describe the use of plasticizers as carrier elements. In an improvement on such patents, U.S. Pat. Nos. 3,705,938 and 3,864,468 teach that surface loss from a plasticized matrix is subject to control through the use of a regulating membrane at said surface.

The controlled-release art has been generally confined to the incorporation and release of insecticides, bactericides, molluscicides and other toxic materials of an organic nature from an elastomer, wherein solubility is essential, or plasticized plastics, wherein an additive carrier material is critical. Microencapsulation processes, wherein an inner core of the toxic agent is surrounded by a polymeric matrix, is well known to the pest control art. In general, release is effected by the rupture of the enveloping membrane.

Little work has been hitherto performed in the development of efficacious long lasting fertilizing systems. U.S. Pat. No. 3,748,115 teaches that plant nutrients can be bound in a matrix of synthetic rubber, waxes, asphalt, and the like. In this work, four critical elements of the invention are set forth. The fertilizer, emphasizing bulk materials and not trace nutrients, must be uniformly dispersed in a hydrophobic binding element. The dispensing unit must be cylindrical in shape. Said cylinder must be partially coated with a water-insoluble, water-permeable exterior membrane. A portion of the cylinder must be non-coated with said membrane. U.S. Pat. No. 3,520,651 extends this art to reach that more than one nutrient can be incorporated in similar dispensing commodities.

Of course, fertilizing materials have long been compounded with various binders to facilitate dispersal and, in some cases, to prolong availability by slowing the rate of solution in water through precluding immediate nutrient element contact with water. U.S. Pat. No. 3,336,129 teaches that the use of small amounts of water insoluble copolymers and terpolymers of ethers, substituted ethers, ethylene oxide, and the like, will serve as carriers for fertilizing materials, said copolymers and terpolymers must be crosslinked. Materials are comprised of polymer+fertilizer+water+soil components and the plant is grown within this medium.

Also, fertilizers such as urea can be coated in a granular form as taught in U.S. Pat. No. 3,336,155, thus retarding solution in ground waters. U.S. Pat. No. 3,276,857 teaches that a fertilizer can be encapsulated with asphalt or various waxes and, thus, emission into the environment is slowed.

Other encapsulated patents include Japanese Pat. No. 4,428,457 wherein a granulated fertilizer leaches through a thin film; U.S. Pat. No. 3,059,379 wherein a fertilizer is encapsulated with the encapsulating film having holes or apertures therein; and U.S. Pat. No. 4,019,890 wherein granular fertilizers are coated with a water-resisting layer and forming a jelly-like gel coating thereon. U.S. Pat. No. 2,891,355 relates to coating shredded styrofoam with a solution of fertilizers and nutrients, adding water, and potting a plant therein. British Pat. No. 68,127 relates to utilizing very small amounts of a thermoplastic material as a binder to prevent bulk fertilizers such as urea, and other deliquescent nitrogen compounds from sticking together. Other patents in the area which do not relate to the present invention are Japanese Pat. No. 4,943,776 and U.S. Pat. Nos. 3,794,478; 2,791,496; 2,797,985; 3,372,019; and 4,111,684.

Turning to the area of larvicides, Boike et al. has shown in examining 23 different organotin formulations and solute elastomer formulations that they were not effective under practical use conditions due to the presence of natural or organic substances common to water courses. Said organic materials rapidly absorb organotin molecules, essentially removing them from mosquito larva contact. In a text by Cardarelli, 1976, it was taught that pesticides in an elastomer matrix can cause a slow-long duration release of the pesticide.

U.S. Pat. No. 4,012,347 relates to a rosin composition containing a film forming polymer, a solvent, and a pigment in which the rosin slowly flakes off, thereby exposing an organotin compound. U.S. Pat. No. 3,234,032 also relates to anti-fouling marine coating compositions wherein various organotin compounds are contained in waxes, oils, or paints. U.S. Pat. No. 3,236,739 relates to a bis(tributyltin)-adipate anti-fouling composition wherein the tin compound is dispersed in substantially water-insoluble film forming vehicles such as spar varnish, vinyl acetate-vinyl chloride copolymer paints, and the like.

In an article appearing in CHEMICAL ABSTRACTS, 75:97577c (1971), various non-organotin liquid pesticides are dispersed in various film-forming polymers, however, the system does not contain a porosigen or a water release system.

U.S. Pat. No. 4,010,141 relates to an organotin compound having a normal-dodecyl side chain such that the tin compound is soluble in and has bleedability from a thermoplastic. However, this patent fails to teach the use of a porosigen and actually teaches away from applicant's invention.

DISCLOSURE OF INVENTION

Accordingly, it is an object of the present invention to provide for the slow release of compounds from a plastic dispenser.

It is yet another object of the present invention to provide for the slow and/or controlled release of a compound from a dispenser, as above, containing a thermoplastic matrix or a thermoset plastic matrix.

It is yet another object of the present invention to provide a dispenser, as above, containing a non-soluble thermoplastic or a thermoset plastic matrix.

It is yet another object of the present invention to provide for the slow release of compounds from a thermoplastic dispenser, as above, wherein said thermoplastic includes polyethylene, low density polyethylene and high density polyethylene, ethylene-vinyl acetate copolymer, polypropylene, polystyrene, polyvinyl acetate, polyamide, polyester, polyurethane, and combinations thereof.

It is another object of the present invention to provide for the slow release of compounds from a thermoset dispenser, as above, containing a thermoset such as phenolic, epoxy, amino resins, unsaturated polyesters, urethane foams, silicone polymers, and combinations thereof.

It is yet another object of the present invention to provide for the slow release from a dispenser, as above, of trace nutrient compounds.

It is yet another object of the present invention to provide for the slow release of trace nutrients, as above, wherein said trace nutrients include zinc, iron, copper, boron, manganese, molybdenum, magnesium, cobalt, chromium, and selenium.

It is yet another object of the present invention to provide for the slow release from a dispenser, as above, of plant regulants.

It is yet another object of the present invention to provide for the slow release from a dispenser, as above, of a pesticide.

It is yet another object of the present invention to provide for the slow release from a dispenser, as above, wherein said compound can be a plant regulant, a nematicide, a soil insecticide, a cercariacide, a molluscicide, an insect larvicide, and the like.

It is yet a further object of the present invention to provide for a slow release aquatic pesticide, as above, wherein said pesticide destroys various aquatic pests such as mollusks, insect larva, trematode larva, and the like.

It is yet another object of the present invention to provide a slow release plastic dispenser, as above, wherein said pesticide includes trialkyl organotin, Temephos, Malathion, Lindane, Sevin, Rotenone, Dichlovos, and the like.

It is yet another object of the present invention to provide a slow release plastic dispenser, as above, wherein said dispenser releases nematicides or soil insecticides.

It is yet another object of the present invention to provide a slow release nematicide or soil insecticide dispenser, as above, where the nematicide includes Dasanit, Ethoprop, Dichlofenthion, Bromophos, and wherein said soil insecticide includes Aldrin, Chlorodane, Carbofuran, Phorate, Terbufos, and the like.

It is a further object of the invention to provide a slow release plastic dispenser, as above, wherein said porosigen has a solubility in water of less than 0.1 or 0.001 grams per 100 grams of water but usually greater than 0.0005 grams per 100 grams of water.

it is still another object of the present invention to provide a slow release plastic dispenser, as above, containing a porosigen having a solubility of from about 0.1 grams per 100 grams of water to about 100 grams per 100 grams of water.

It is yet a further object of the present invention to provide a slow release plastic dispenser for releasing a pesticide in an aqueous environment, as above, wherein said dispenser floats.

It is yet another object of the present invention to provide a slow release floating dispenser, as above, which may be in any of several forms, such as anchored strands, anchored chips, bimodal or polymodal pellets, and the like.

It is yet another object of the present invention to provide a floating dispenser, as above, so shaped such that it is not covered during release over a period of months by various items such as silt, debris, and the like.

It is yet another object of the present invention to provide a floating thermoplastic dispenser, as above, wherein said floating dispenser may be attached to an anchor, as though a connecting member, for example, a line, or the like.

These and other objects of the present invention will become apparent from the following specification.

Generally, a controlled release plant nutrient dispenser, comprises: 100 parts by weight of a polymer matrix, said polymer matrix made from a compound selected from the group consisting of a thermoplastic, a thermoset polymer, and combinations thereof; and a plant nutrient, the amount of plant nutrient ranging from about 10 to about 160 parts by weight per 100 parts of said polymer matrix and being dispersed through said polymer matrix so that upon contact of the dispenser with soil moisture, the plant nutrient is released at a rate required by the plant to stimulate growth.

Generally, a process for the controlled release of a plant nutrient from a dispenser, comprises: adding and mixing 100 parts by weight of a polymer, and from about 10 to about 160 parts by weight per 100 parts of said polymer matrix of a plant nutrient, said polymer selected from the group consisting of a thermoplastic, a thermoset polymer, and combinations thereof; forming a polymer matrix containing said plant nutrient contained throughout said matrix, thereby forming a dispenser; and applying and contacting said dispenser with soil so that upon contact with moist soil said plant nutrient will be released at a rate required by the plant to stimulate growth.

Generally, the controlled release of a soil compound from a dispenser, comprises: 100 parts by weight of a polymer matrix; a soil compound, said soil compound dispersed in said polymer matrix, said polymer matrix made from a polymer selected from the group consisting of a thermoplastic polymer, a thermoset polymer, and combinations thereof; a porosigen, and porosigen dispersed in said polymer matrix; the amount of said porosigen ranging from about 1 to about 80 parts by weight per 100 parts of polymer, said porosigen having a solubility of less than 100 grams per 100 grams of water, said soil compound selected from the group consisting of a plant regulant, a nematicide, a soil insecticide, and combinations thereof.

Additionally, a process for the controlled release of a soil compound from a dispenser, comprises the steps of: adding and mixing 100 parts by weight of a polymer, from about 4 to about 60 parts of a soil compound by weight per 100 parts of said polymer, and from about 5 to about 80 parts of a porosigen by weight per 100 parts of said polymer, said polymer selected from the group consisting of a thermoplastic polymer, a thermoset polymer, and combinations thereof, said soil compound selected from the group consisting of a plant regulant, a nematicide, a soil insecticide, and combinations thereof, said porosigen having a solubility of less than 100 grams per 100 grams of water; forming a polymer matrix containing said soil compound and said porosigen dispersed throughout said matrix and thereby forming a dispenser; and applying and contacting said dispenser to soil so that upon contact with moist soil, said soil compound is released.

Generally, a floating controlled release pesticide dispenser, comprises: 100 parts by weight of a polymer matrix, said polymer of said polymer matrix selected from the group consisting of a thermoplastic polymer, a thermoset polymer, and combinations thereof; a pesticide, said pesticide dispersed in said polymer matrix, said pesticide being a pesticide for destroying aquatic pests in an aqueous environment, the amount of said pesticide ranging from about 2 parts by weight to about 80 parts by weight per 100 parts of said polymer except when said pesticide is an organotin compound, the amount of said organotin compound ranging from about 25 to about 75 parts; a porosigen, said porosigen dispersed in said polymer matrix, said porosigen slowly releasing said pesticide from said polymer, said dispenser having a density of less than 1.0 grams per cc; and an anchor, said anchor having a density of greater than 1.0 grams per cc and connected to said dispenser.

Additionally, a controlled release pesticide dispenser, comprises: a polymer matrix, the amount of said polymer being 100 parts by weight, said polymer selected from the group consisting of a thermoplastic polymer, a thermoset polymer, and combinations thereof; a pesticide, said pesticide dispersed in said polymer matrix, said pesticide being a pesticide for destroying aquatic pests in an aqueous environment, the amount of said pesticide ranging from about 2 parts to about 80 parts by weight per 100 parts of said polymer, except when said pesticide is an organotin compound, the amount of said organotin compound ranging from about 25 to about 75 parts; and a porosigen, said porosigen dispersed in said polymer matrix, said porosigen slowly releasing said pesticide from said polymer, said porosigen having a solubility of 100 grams or less per 100 grams of water.

Generally, a process for the controlled release of a pesticide from a floating dispenser, comprises the steps of: adding and mixing 100 parts by weight of a polymer, from about 2 to about 80 parts by weight per 100 parts of polymer of a pesticide except when said pesticide is an oganotin compound, the amount of said organotin compound ranging from about 25 to about 75 parts, and a porosigen, said polymer selected from the group consisting of a thermoplastic polymer, a thermoset polymer, and combinations thereof; forming a floating polymer matrix dispenser, said dispenser having a density of less than 1.0 grams per cc; and attaching said dispenser to an anchor, said anchor having a density of greater than 1.0 grams per cc.

Additionally, a process for slowly releasing a pesticide compound from a dispenser comprises the steps of: adding and mixing 100 parts by weight of a polymer, a pesticide for use in an aqueous environment for destroying aquatic pests, and a porosigen having a solubility of 100 grams or less per 100 grams of water, the amount of said pesticide ranging from about 2 parts to about 80 parts by weight per 100 parts of said polymer, except wherein said pesticide is an organotin compound, the amount of said organotin compound ranging from about 25 parts to about 75 parts by weight per 100 parts of said polymer; and forming a polymer matrix dispenser so that upon contact with an aqueous environment, said pesticide is slowly released therefrom.

BEST MODE FOR CARRYING OUT THE INVENTION

Figure 1:
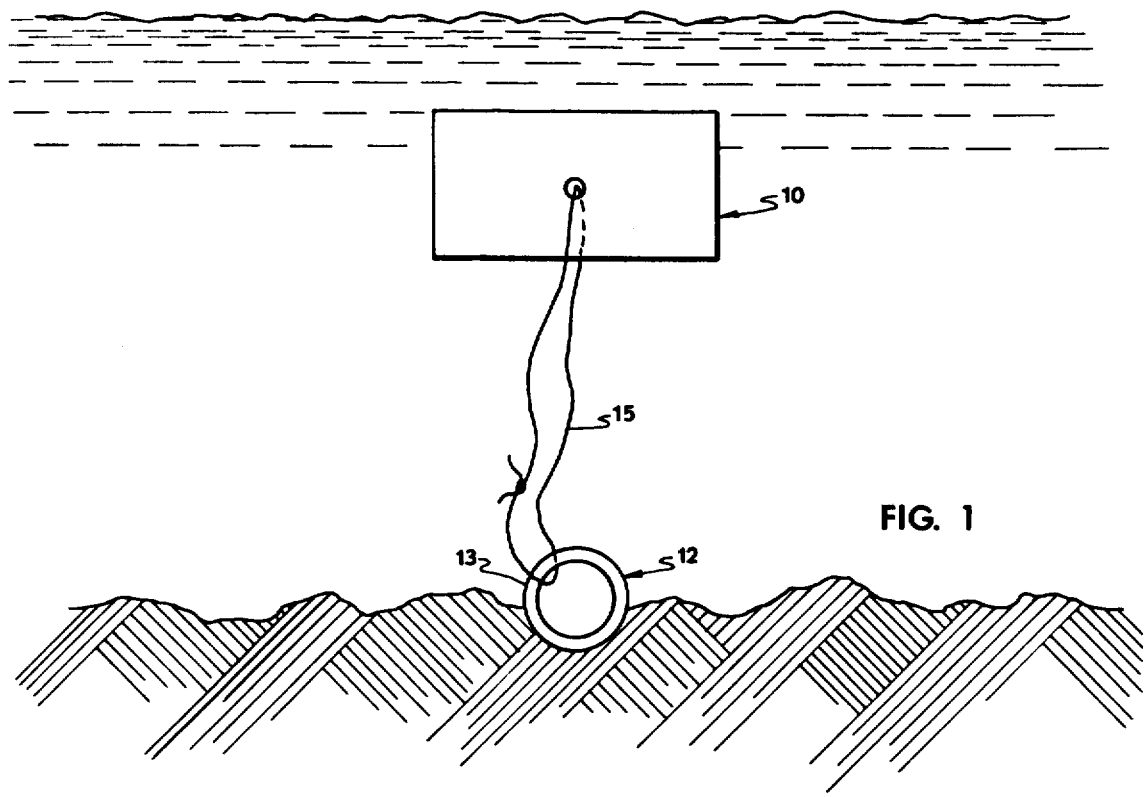
FIG. 1 is an elevational view showing a floating chip attached via a line to a weighted anchor which is resting on the bottom of a body of water.
Figure 2:
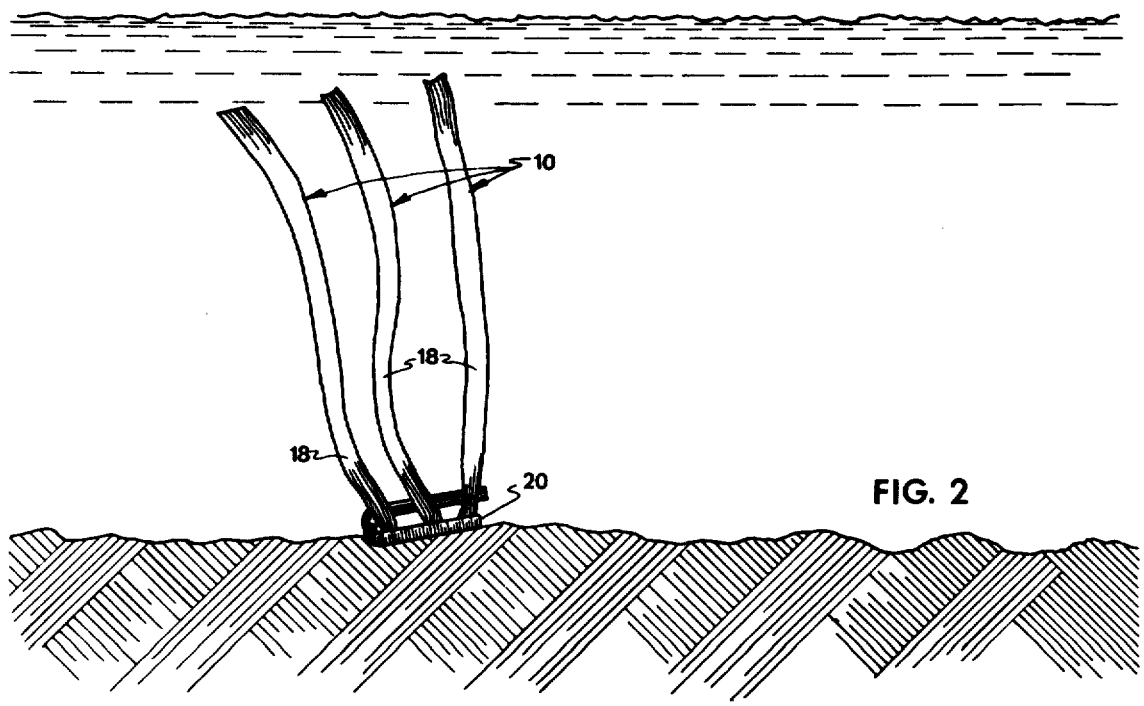
FIG. 2 is an elevational view wherein a floating pesticide dispenser is in the form of strands which are attached to a weighted anchor as in the form of a metal clamp.
Figure 3:
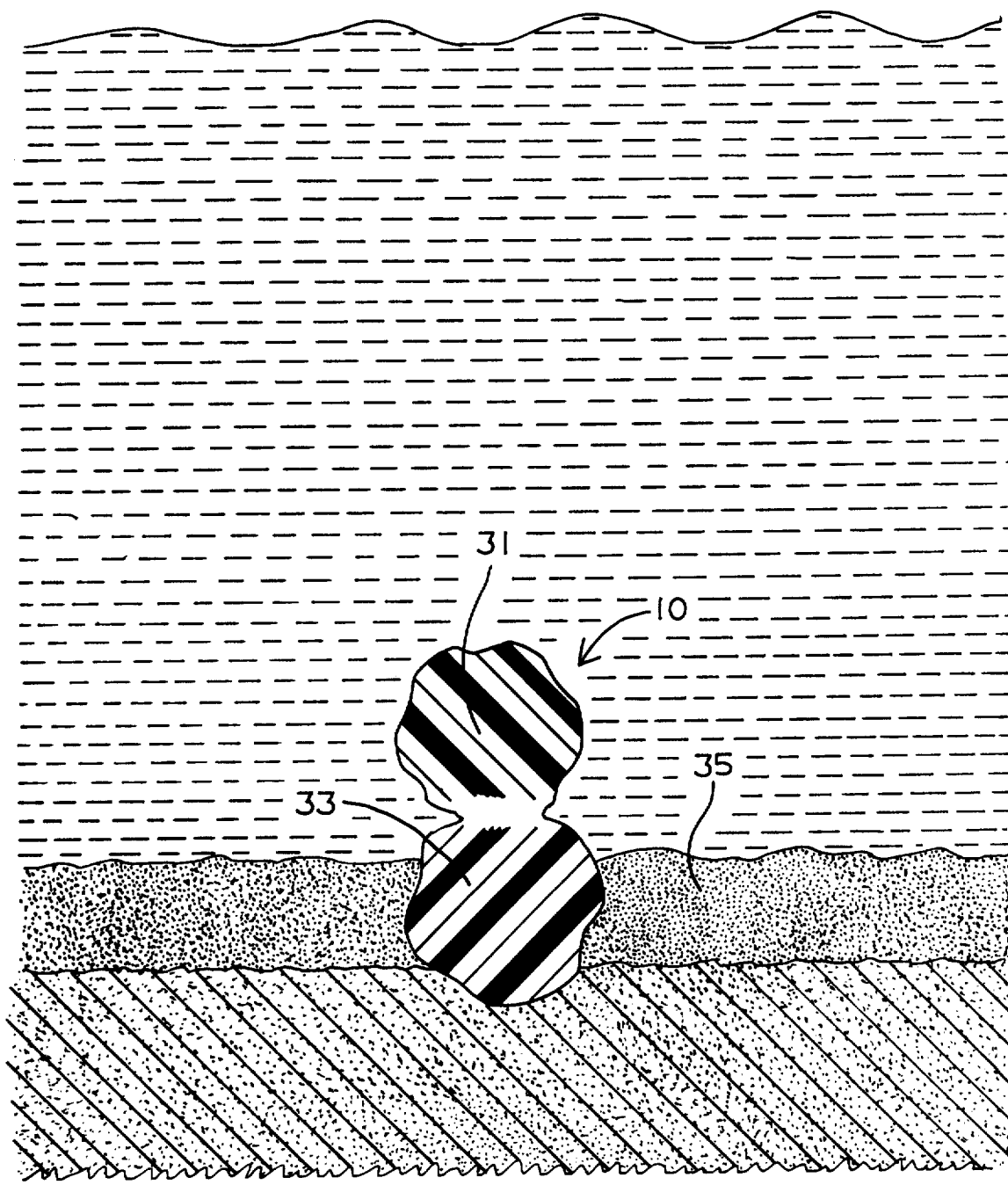
FIG. 3 is an elevational view showing a bimodal pellet having an anchor end and a floating end such that said floating end resides above the bottom of a body of water.

The present invention relates to a sustained, controlled, or slow release of a compound upon contact with water from a thermoplastic dispenser or a thermoset dispenser generally containing a porosigen compound, and compounds either for the release of trace nutrients, or plant growth regulators, or nematicides, or soil insecticides, or molluscicides, or cercariacides, or aquatic larvicides, upon contact with water, either in an aquatic environment or as in moist soil.

In my prior copending continuing applications, my inventions relate to the sustained release of various pesticides, from a thermoplastic matrix, or dispenser, against such aquatic pests such as mosquito larva, the aquatic larva form of parasites, molluscan hosts of trematode parasites, and the like. Furthermore, my prior specifications set forth the various specific pesticide compounds and the fact that the pesticide could be contained in a thermoplastic matrix which floated, that is, did not sink. Furthermore, my prior invention related to the use of a trace nutrient in the thermoplastic matrix so that upon contact with moisture, such as moisture from soil, the trace nutrient would be released and thereby stimulate plant growth. The exact nature of the various pesticides, various porosigens, as well as the trace nutrients contained within the thermoplastic matrix, as well as th concepts of the invention therein, are set forth in my previous continuing applications which are hereby fully incorporated by reference, with regard to all pertinent and essential matter. It is furthermore noted that all my previous continuing applications are incorporated by reference due to the length of the various specifications, but that various portions thereof will be set forth hereinbelow.

Considering first the thermoplastic polymers, that is polymers which soften and flow when heat and/or pressure is applied (the changes being reversible), they are well known to the art and are readily set forth in various references such as textbooks, journals, various encyclopedias, and the like, as for example, the various thermoplastics set forth in the MODERN PLASTICS ENCYCLOPEDIA, 1979-1980, Vo. 56, 10A, McGraw-Hill, as well as in other years, and the like, which are hereby fully incorporated by reference. Furthermore, the various properties thereof are well known as are the molecular weight distributions. For example, the number average molecular weight can range from about 10,000 to about 1,000,000, desirably from about 40,000 to about 500,000, and preferably from about 60,000 to about 250,000. Various thermoplastics can be utilized so long as a solid dispenser or plastic matrix is formed. However, it is noted that if a thermoplastic is soluble in water, it is not desired or a part of the present invention since the thermoplastic matrix dispenser will readily and rapidly degrade and not permit slow release over an extended period of time. Generally, thermoplastics which can be used include the various following thermoplastics, as well as common copolymers or terpolymers thereof. The various polyolefins containing from 2 to 10 carbon atoms. Specific examples include polyethylene, such as low density and high density polyethylene. Typically, low density polyethylene has a partially (approximately 50 to approximately 60 percent) crystalline solid structure, whereas high density polyethylene typically has over a 90 percent crystalline structure. Polypropylene can also be utilized. Additionally, various copolymers of ethylene may be utilized such as ethylene-propylene, and copolymers of ethylene and vinyl acetate.

An example of an ethylene-vinyl acetate copolymer includes those wherein the amount by weight of the ethylene units, based upon the total weight of the copolymer, ranges from about 60 percent to about 95 percent with a range of from about 80 percent to about 93 percent being preferred. The weight average molecular weight of the copolymer generally ranges from about 40,000 to about 400,000 and preferably from about 75,000 to about 300,000. Desirably, the copolymer has an ASTM Test #D1238 melt flow index of from about 6 to about 12 and preferably from about 7 to about 11 and a Vicat softening point of from about 70° C. to about 95° C. Since, apparently, the ethylene repeating units in the copolymer act as a regulator with regard to pore size, higher amounts of the ethylene constituent will result in slower release times.

An example of an ethylene-propylene copolymer is those having a weight average molecular weight of from about 50,000 to about 250,000 with a preferred range of from about 100,000 to about 200,000. The percent by weight of the ethylene units can generally vary from about 30 percent to about 80 percent and preferably from about 45 percent to about 75 percent. The melt flow index of the ethylene-propylene copolymer can generally range from about 15 to about 45, and preferably from about 20 to about 32 according to ASTM Test #1238 at 190°, 21600 gm,gm/10 minutes.

Moreover, in order to promote long release duration, it has been found useful, although not necessary, to blend the ethylene-vinyl acetate copolymer or the ethylene-propylene copolymer, or combinations thereof, with a polyethylene, especially low density polyethylene (that is, a density of from about 0.90 to 0.94 g/cc), having a melt flow index similar to said ethylene-vinyl acetate copolymer, that is from about 5 to about 14 and, preferably, from about 7 to about 11, and a weight average molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight based upon the total weight of the blend of the ethylene-vinyl acetate copolymer, or the ethylene-propylene copolymer, or combinations thereof, and the polyethylene.

Polystyrene can be utilized as well as a family of styrene polymers which includes copolymers of styrene with other vinyl monomers or vinyl substituted aromatics having from 8 to 12 carbon atoms, polymers of derivatives of styrene, and the like. Thus, poly-alpha-methylstyrene may be utilized. Another group of thermoplastic polymers is the acrylic polymers with specific examples being polyacrylate, polymethylacrylate, and polymethylmethacrylate. The polyvinyl esters constitute yet another group with a specific example being polyvinylacetate. Still another group is the polyvinyl acetals such as polyvinylbutyral. The phenylene oxide-based thermoplastics can also be used. The various chlorine-containing polymers can be utilized such as polyvinylchloride, polytetrafluoroethylene, polychlorotrifluoroethylene, polyvinylfluoride, polyvinylidenefluoride, and the like. These polymers are used without plastication.

The polyamides or nylons are another group of thermoplastics and include Nylon 6, Nylon 10, Nylon 11, Nylon 12, Nylon 6,6, Nylon 6,10, and the like. Polyethers such as polyoxymethylene can be utilized. Another large group of thermoplastic compounds are the polyesters such as polyethylene terephthalate, polybutylene terephthalate, and the like. The polyurethanes constitute yet another group of thermoplastics. As known to those skilled in the art, the polyurethanes can be made from several types of polymers or prepolymers. The cellulose plastics are yet another group with specific examples being cellophane and rayon.

Desired thermoplastics include polyethylene, including low density polyethylene and high density polyethylene, copolymers of ethylene-vinyl acetate, polypropylene, polybutylene, polystyrene, poly-alpha-methyl styrene, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, a copolymer of ethylene-propylene, polyvinylidene fluoride, Nylon-6, Nylon-6,6, Nylon-6,10, polyoxymethylene, polyethyleneterephthalate, cellophane, rayon, and combinations thereof. Highly desired polymers include polyamide, polyvinyl acetate, polyurethane, and combinations thereof.

Preferred thermoplastics include polyethylene (including low or high density polyethylene), a copolymer of ethylene-vinyl acetate, polystyrene, polypropylene, polyester, and combinations thereof.

The various plastic compounds generally referred to as thermoset compounds can also be utilized.

Thermoset compounds are generally defined as those which change irreversibly under the influence of heat from a fusible and soluble material into one which is infusible and insoluble through the formation of a covalent crosslinked, thermally stable network. The thermoset compounds or resins are furthermore those in which crosslinking occurs simultaneously with the final steps of polymerization, regardless of the amount of heat required in this step. Thus, the thermoset, the porosigen, and the compound to be slowly released are thoroughly mixed or dispersed and then heated, whereupon a thermoset matrix is formed. The matrix, if need be, is then reduced to an appropriate size through any conventional method, e.g., a pelletizer, whereupon a suitable dispenser is formed.

Thermoset compounds are well known to those skilled in the art and are set forth in various texts, encyclopedias, journals, etc., such as the MODERN PLASTICS ENCYCLOPEDIA, 1979-1980, Vol. 56, No. 10A, McGraw-Hill, which is hereby fully incorporated by reference. Examples of thermoset compounds include the various phenolic resins, the various amino resins such as melamine and the like. The unsaturated polyester resins may also be utilized as can the various epoxy resins. Still further, the various urethane foams which are crosslinked may be utilized as can the silicon polymers. Also, the various thermoset polyimides can be used. Generally, specific thermosets which can be used include conventional and known compounds, such as those set forth in various texts, encyclopedias, and the like.

Naturally, any of the above thermoplastics and thermosets may be utilized including combinations thereof. It is generally desirable to use the low cost compounds. Of the thermosets, the various phenolics and the various epoxies are preferred.

The various trace elements utilized are generally in the form of salts or oxides, which are readily available, desirably low in cost, and are not highly deliquescent. It is noted that the term "salts" includes the various hydrates thereof, that is the mono-, the di-, the tri-, the tetra-, the penta-, the hexa-, the hepta-, etc. Should the salt not exist in the non-hydrate form, the most common forms are meant. With regard to zinc-containing compounds which may be utilized as trace nutrients, they include the following: zinc sulfate, zinc chloride, zinc carbonate, zinc oxide, zinc phosphate, zinc chlorate, zinc nitrate, the various existing hydrates thereof, and the like. Typical copper trace nutrient compounds include copper sulfate, copper carbonate, copper oxide, copper oxychloride, copper nitrate, copper phosphate; various copper complexes such as tetraamines, diamines; the various existing hydrates thereof, and the like. Typical iron trace nutrient compounds include iron chloride, iron sulfate, iron oxide, the various existing hydrates thereof, and the like. Typical manganese trace nutrient compounds include manganese oxide, manganese sulfate, manganese chloride, manganese nitrate; the various existing hydrates thereof, and the like. Typical boron trace nutrient compounds include boric acid, sodium biborate; the various hydrates thereof, and the like. Typical molybdenum trace nutrient compounds include molybdenum oxide, sodium molybdate, potassium molybdate, the various existing hydrates thereof, and the like. Typical cobalt trace nutrient compounds include cobalt sulfate, cobalt chlorate, cobalt nitrate; the various existing hydrates thereof, and the like. Typical selenium trace nutrient compounds include sodium selenate, selenium dioxide, selenium trioxide, selenium disulfide, selenium sulfur oxide, and the like. Typical magnesium compounds include magnesium carbonate, magnesium sulfate, magnesium nitrate, magnesium acetate, magnesium oxide, magnesium chloride, magnesium ammonium chloride, magnesium phosphate, magnesium sulfite, the various existing hydrates thereof, and the like. Typical chromium compounds include chromium (II) sulfate, chromium chloride, chloropentammine chromium chloride, the various hydrates thereof, and the like.

Desirably, the amount of trace nutrient released by the polymer dispenser is such to make a plant grow, to stimulate plant or animal growth, and to supplement the environment. Thus, exact amount will vary from site to site, soil to soil, crop to crop, animal to animal, and the like. As approximate rule of thumb, the dispenser or mixture can contain from about 1 percent to about 60 percent by weight of a particular trace nutrient ion based upon the total weight of the dispenser, pellet, etc. From about 2 to about 50 percent is desirable, with from about 4 to about 40 percent being more desirable. The amount of trace nutrient generally ranges from about 10 to about 160 parts by weight based upon 100 parts by weight of the polymer, desirably from about 25 to about 125, and preferably from 50 to about 100 parts by weight. Naturally, more than one trace nutrient may be utilized in the dispenser and thus several may be utilized. Furthermore, since some of the trace nutrients serve as a porosity agent itself, it is not always necessary to utilize a porosigen, although a porosigen is generally preferred, and will hasten the release rate. Trace nutrients, which have a fair degree of solubility, include zinc sulfate, zinc chloride, copper sulfate, copper oxychloride, iron sulfate, iron chloride, manganese sulfate, manganese chloride, boric acid, sodium biborate, sodium molybdate, cobalt sulfate, and sodium selenate.

Controlled release trace nutrients are usually added directly to the soil by conventional application means. Selection is based upon need as well as the particular nature of the soil. For example in alkaline soil needing iron, a choice selection would be an iron salt soluble in the alkaline range, whereas in acid soil, the selection would be a salt soluble in the acid pH range. Since release is dependent upon soil moisture, a hygroscopic material such as calcium chloride which attracts moisture can be utilized as a matrix additive for use in dryer soils. The range of the hygroscopic material is from about one half to about 25 and preferably from about 1 to 5 parts by weight per 100 parts of polymer. Examples of specific hygroscopic compounds include $P_2O_5$, $Mg(ClO_4)_2$, KOH, $Al_2O_3$, and Ba $(ClO_4)_2$. Also, additives such as lime might be similarly added to the matrix in order to change the soil pH in the immediate vicinity of the dispenser in order to induce more rapid trace nutrient release and plant absorption.

Controlled release trace nutrients are not only of value to crop production, but also to pasturage, forestry, horticulture, and the like, and such uses are hereby implied.

Controlled release trace nutrients may also be added directly to livestock production, such as beef cattle, poultry, sheep, swine, and the like, as an additive to feed.

Pesticides are compounds which kill things undesirable to man, for example, animals, such as insects, and the like. Various pesticides are effective against aquatic pests such as mosquito larva, black fly larva, midge larva, the molluscan hosts of trematode parasites, for example, snails, and some cases the aquatic larva forms of such parasites, and the like. Examples of pesticides which are effective against aquatic animal pests include tetramethyl-O,O'-thiodi-p-phenylene phosphorothioate (commonly referred to as Temephos), an organotin compound having the formula $R_3S_nX$, wherein $R_3$ is an alkyl group having from 1 to 8 carbon atoms, desirably from 3 to 6 carbon atoms, and preferably 3 carbon atoms, that is, propyl and the isomers thereof being preferred. An alkyl group having 4 carbon atoms, that is butyl, and the various isomers thereof is highly preferred. Additionally, the organo portion R of the tin toxicant may be an aryl group or a substituted aryl group with the substituted portion being an alkyl or an ester group containing from 1 to 6 carbon atoms. Specific examples of such compounds include phenyl, phenyl acetate, phenyl propionate, phenyl isobutyrate, and the like.

The anion or "X" portion of the organotin compound can be a halogen, an oxide, an alkoxy $OR^1$, wherein $R^1$ is an alkyl and contains from 1 to 12 carbon atoms, or an group where R" is an alkyl having from 1 to 12 carbon atoms, such as propionate, butyrate, pentyate, hexylate, and the like, with acetate being preferred. Of the various anions, the halogens are preferred with fluorine being highly preferred. Thus, tributyltin fluoride is preferred, with tributyltin acetate, triphenyltin fluoride, tributyltin oxide, and triphenyltin acetate being desired compounds.

Another effective pesticide is 2-(1-methylethoxy)-phenol methylcarbamate, commonly known as Baygon, manufactured by Mobay Chemical Company of Kansas City, Mo., O,O-diethyl-O-(3,5,6-trichloro-2-pyridl)-phosphorothioate, commonly known as Dursban; and the O,O-dimethyl phosphorodithioate ester of diethyl mercaptosuccinate, commonly known as Malathion. These compounds, along with Temephos, Dibrom and Fenitrothion are preferred. Other examples include Dibrom or Naled (dimethyl-1,2-dibromo-2,2-dichloroethyl phosphate; Thiodan, i.e., 6,7,8,9,10,10a-hexachloro-1,5,5a,6,9,9a-hexahydro-6,9-methano-2,4,3-benzodioxathiepen-3-oxide; Lindane, that is Gamma-1,2,3,4,5,6-hexachlorocyclohexane; Sevin, that is 1-naphthyl methylcarbamate; Propoxur, that is, 2-(1-methylethoxy)phenol methylcarbamate; Rotenon, that is, 1,2,12,12a-tetrahydro-2-isopropenyl-8,9-dimethoxy-(1)-benzopyrano-(3,4,6)-furo-(2,3,6)(1)-benzopyran-6(6aH) one; DDT, that is, dichlorodiphenyltrichloethane; Methoxychlor, that is, 2,2-bis(p-methoxyphenyl)-1,1,1-trichloroethane; Dimilin, that is, N-[(4-chlorophenyl)(amino)(carbonyl)]-2,6-difluorobenzamide; Dichlorvos, that is, dimethyl 2,2-dichlorovinyl phosphate; Fenitrothion, that is, O,O-dimethyl,O-(3-methyl-4-nitrophenyl)phosphorothioate; Fenthion, that is, O,O-dimethyl-O-[3-methyl-4-(methylthio)(phenyl)]phosphorothioate; Dimethoate; that is, O,O-dimethyl-S-(N-methylcarbomoyl methyl)phosphorodithioate; Methidathion (Suprocide), that is, O,O-dimethyl phosphorodithioate, S-ester with 4-(mercaptomethyl)-2-methoxy-1,3,4-thiodiazoline 5-one; and, Temephos, that is, O,O,O,'O'-tetramethyl-O,-O-thiodi-p-phenylene phosphorothioate.

Based upon 100 parts of the polymer dispenser, that is the thermoplastic or the thermosetting compound, the amount of the aquatic pesticide ranges from about 2 parts to about 70 or 80 parts by weight, desirably from about 3 parts to about 50 parts, and preferably from about 5 parts to about 20 parts by weight. However, when the aquatic pesticide is an organotin compound, the amount is from about 25 to about 75 parts with from about 40 to about 70 parts being preferred.

The dispenser of the present invention with regard to the aquatic pesticide may be applied to any aquatic environment such as ponds, lakes, rivers, streams, swamps, waterways, and the like.

However, such bodies of water will often fill up with silt, debris, and the like, thereby covering the dispenser, as in the form of a pellet, granule, or the like, and thereby adversely affecting release. On the other hand, it can be washed away. Thus, it is desirable to incorporate the thermoplastic or thermosetting dispenser in a floating form connected to an anchor. In such a manner, the dispenser will reside above the bottom of an aquatic body of water and effectively operate for the entire life of the dispenser.

The floating dispenser should have a density of less than 1.0 grams per cc, that is a specific gravity less than 1.0. The density can be controlled through proper selection of components including polymers, that is, thermoplastics or thermoset, lightweight fillers, as well as the use of common and conventional blowing agents known to those skilled in the art. Often, the density of the dispenser will be less than 1.0 grams per cc and thus not require such additives. Generally, any conventional foaming or blowing agent, as well as lightweight filler may be utilized. Examples of specific blowing agents well known to the art, include the various known and conventional foaming or blowing agents, as well as those set forth in various texts, journals, encyclopedias, and the like, such as for example those set forth in MODERN PLASTICS ENCYCLOPEDIA, as noted above, which is hereby fully incorporated by reference. The amount of the blowing or foaming agent is simply that required in order to make the dispenser float. This is usually a very small amount and may vary from about 0.05 to about 2 parts by weight per 100 parts of polymer, with from about 0.1 to about 1.0 parts being preferred. A suitable blowing agent is Celogen. This blowing agent, as with all other desired blowing agents, degrades by release at a temperature at which the floating pesticide dispenser or composition can be extruded without degrading the components thereof. The gas creates a series of gas filled voids within the matrix. Other blowing agents include Celogen OT, Celogen RA, and the like which release nitrogen and/or carbon dioxide and/or carbon monoxide upon the application of heat thereto. Still other materials include liquids that vaporize at extrusion temperatures such as dichloroethane, or carbon dioxide releasing materials such as various bicarbonates, or nitrogen releasing chemicals such as azodicarbonamide, and N,N'-dinitrosopentamethylenetetramine.

Instead of a foaming or blowing agent, a lightweight filler may be utilized. Again, such lightweight additives are known to the art and include materials such as microballoons (e.g., phenolic), powdered nut shells, corn cob, wood dust, and the like. Once again, the amount required is that such that the dispenser will float. Generally, the amount may vary from about 3 to about 25 parts by weight with preferably from about 5 to about 15 parts by weight per 100 parts of polymer. Furthermore, it is noted that various thermoplastics or thermosets may also be utilized often times without any filler or blowing agent, since they often have a very low density of less than 1.0 grams/$cm^3$, as, for example, low density polyethylene, and other polymers.

In order to ensure that the floating dispenser is not washed or floated away in various environments, but generally contained in a confined area, it has an anchor. The anchor should be of a weight such as to prevent it from floating away in the intended area of use. Generally, the density of the anchor is in excess of 1.5, desirably in excess of 2.7 grams per cc and the total weight is often in the range of from about 2 to about 10 or 5 to 50 times the total weight of the floating dispenser. Of course, depending upon the actual use situation, the anchor weight may be less than this range or even a specific gravity of 1.5 or 2.7 grams per cc as when utilized in an area of slow moving or stagnant water, for example, a swamp, or in excess of this weight if utilized in an area of fast moving water, for example, a brook, stream, drainage ditch, catch basin, etc.

A specific embodiment of the floating dispenser is disclosed in FIG. 1 wherein the floating dispenser is generally indicated by the numeral 10, with the anchor generally indicated by the numeral 12 which may be in the form of a weight 13. A string, line, or any other suitable connecting means 15 extends and connects the floating dispenser or chip and the anchor. The density of the anchor, as noted above, is generally in excess of 1.5 or 2.7 grams per cc and may be an item such as steel, for example, a washer, a metal crimp, generally any other metal, or other item which serves as a suitable ballast. Desirably, the length of line is such as to preclude silting over due to input of various sorts of debris, in the particular aqueous environment.

The floating pesticide dispenser, as shown in FIG. 1, thus resides within the aqueous body and can be made to reside within the infraneustral zone where mosquito larva spend most of their time before emergence, or in the zone where various other aquatic pests such as snails inhabit. Moreover, depending upon the length of connecting line 15, floating pesticide dispenser 10 can be made to always float upon the water surface (not shown) regardless of typical variations in level of the water depth. This factor also affords a visible inspection.

A second structure for suspending a floating controlled release pesticide dispenser is in FIG. 2. In this embodiment, floating pesticide dispenser 10, which has a density of less than 1.0 grams per cc, is processed as an extruded strand, rope, or the like. One or more strands 18 are clamped together through fastener 20 which may be a metal crimp or generally any compound having a density of 1.5 or 2.7 grams or greater as well as a mass greater than that of a total number of extending strands 18. Naturally, strands 18 have a length conducive to their end use, and sufficient to avoid coverage as by slit or debris. The crimp is of suitable geometry, e.g., may have tines or legs, to prevent the strands from washing away as through flooding. Moreover, several strands may be held together as by having an enlarged bottom portion (not shown) so that a mechanical binding occurs at a fastener through which the strands cannot pass. Of course, strands may also be crimped in the center so that one length of strand becomes two strands.

Another structure for a floating release dispenser is shown in FIG. 3. In this Fig., two pellets, granules, etc., are shown. Pellet 31 is a dispenser and it is attached and connected to anchor 33. In this particular drawing, the shape is that of a bimodal pellet, that is two pellets of different densities which have been connected as for example, through heating the pellets to their softening temperature and connecting them together, by melt welding or through the use of adhesives, or any other conventional manner. As apparent from FIG. 3, the bimodal pellet sits above the bottom of a body of water so that any silt, debris, a blocking layer of material, or the like, as indicated by the numeral 35 does not cover the floating portion of the bimodal pellet. The floating portion has a density of less than 1.0 grams per cc, whereas the anchor portion has a density of from about 1.02 to about 1.1 grams per cc. The net effect is that the system floats on silt, sand, mud, etc., and rises as said silt, sand, or mud depth increases with increasing deposition. Although a bimodal structure is shown in FIG. 3, multimodal pellets may exist having a plurality of floating dispenser portions as well as a plurality of anchor portions. Moreover, they may exist in various geometric forms or shapes.

As should be apparent from the above embodiments, generally any type, shape, or form of floating dispenser-anchor arrangement can be utilized within the concepts of the present invention. Moreover, the sizes of the various pellets, strands, anchor, and the like may vary greatly. The connection may be direct as in the bimodal pellet or it may be a connecting line of any suitable material such as a polyester, nylon, fish line, or other water-resistant material. Naturally, the floating dispenser will have incorporated therein the various components as set forth herein.

The type of porosigen, that is, a porosity-inducing agent, can vary depending upon the desired release rate sought. Thus, a porosigen, that is, a porosity-inducing agent, having a moderate or low solubility can be utilized, that is a solubility of approximately 0.1 grams or less per 100 grams of water with a solubility of approximately 0.01 grams or less per 100 grams of water often being desired. The lower limit of solubility is generally that which will give a suitable release rate for a specific application. Such a release rate will vary depending upon the amount of porosigen, the amount and type of compound, e.g., pesticide, the amount of dispenser utilized, and the like, all of which can be readily determined by one skilled in the art. Thus, porosigens can be utilized which are very slightly soluble or barely soluble. Generally, a lower solubility limit of about 0.0005 is desired. Additionally, a porosigen, that is, a porosity-inducing agent, may be utilized which has a solubility of between 0.1 to about 1 gram per 100 grams of water, or from about 1.0 gram, or about 10 grams to about 100 grams per 100 grams of water. That is, a porosigen may be utilized having a solubility in the range of from about 0.1 to about 100 grams per 100 grams of water, or a sub-range thereof. The porosigen, regardless of solubility, may generally be any compound which is inert with regard to the types of polymer, the trace nutrient, the aquatic pesticide, or the type of release compound incorporated therein. That is, by inert, it is meant that the porosigen does not chemically react with the polymer, trace nutrient, pesticide compound, etc., or otherwise render the dispenser ineffective for its intended purpose. Furthermore, it should not be damaging or harmful to the environment in terms of toxicity. The porosigen can generally be any compound which is set forth in the Handbook of Chemistry and Physics, 1977-1978, published by the Chemical Rubber Company, which is hereby fully incorporated by reference, which meets the above requirements with regard to solubility, inertness, and being non-harmful to the environment.

With regard to the low or moderate solubility porosigens, a suitable porosigen includes the inorganic salts or the hydrates thereof, or oxides. The cation of such a salt may generally be any of the alkaline metals and preferably any of the non-toxic alkali or alkaline earth metals, Column 1A and 2A, respectively, of the Periodic Table. Additionally, various other metals may be utilized such as iron, nickel, zinc, tin, silver, and the like. The anion portion of the salt may generally be any negative charge entity, as the various carbonates, the various bicarbonates, the various nitrates, nitrites, or nitrides, the various sulfates, sulfites, or sulfides, the various phosphates, phosphites, or phosphides, including the ortho-, pyro-, hypo-, variations thereof, and the like. Generally, the sulfates, sulfites, and sulfides are preferred as anions, with carbonates being highly preferred. Moreover, as noted above, the anion may be an oxide of the metal. Specific examples of porosigens include magnesium carbonate, magnesium sulfide, magnesium phosphide, magnesium oxide, calcium carbonate, calcium bicarbonate, calcium nitride, calcium oxide, calcium phosphate, calcium phosphite, calcium sulfide, calcium sulfite, iron carbonate, iron sulfate, iron sulfide, iron sulfite, nickel carbonate, nickel sulfide, zinc carbonate, zinc sulfide, zinc sulfite, tin sulfide, tin oxide, silver carbonate, silver oxide, silver sulfide, silver sulfite, sodium bicarbonate, lithium phosphate, beryllium oxide, strontium carbonate, strontium sulfate, and strontium sulfite. Magnesium carbonate and strontium carbonate are preferred, with calcium carbonate being highly preferred.

The inorganic salts, or hydrates, or oxides thereof, of the alkali metals and the alkaline earth metals, Column 1A and 2A, respectively, of the Periodic Table, as well as of nickel, iron, zinc, tin, and silver, having a solubility of at least 0.1 grams/100 grams of water and up to about 100 grams per 100 grams of water can be used. Desirably, the halogen or carbonate salts of these cations can be used, with the chloride salts being preferred. The Handbook of Chemistry and Physics, 1977-1978 Edition, Supra. is hereby fully incorporated as to such specific compounds since the list is rather extensive. Additionally, ammonia as a cation constitutes another class of salts with specific examples being ammonium bromide, ammonium carbonate, ammonium bicarbonate, ammonium chlorate, ammonium chloride, ammonium fluoride, ammonium sulfate, and the like. Of this group, sodium bicarbonate, sodium carbonate, and ammonium sulfate are preferred.

With regard to the amount of porosigen when utilized with the trace nutrients, the range is from 0.1 to about 70 parts by weight based upon 100 parts of the polymer, although up to 100 parts may at times be utilized. If a porosigen is utilized having a solubility of greater than 0.1, that is from about 0.1 to about 100 grams per 100 grams of water, the amount desirably ranges from about 1 to about 30 parts and preferably from about 2 to about 12 parts. If a porosigen has a solubility of less than 0.1 parts or less than 0.01 parts per 100 parts of water, that is down to about 0.0005 grams per 100 grams of polymer, the desired amount ranges from about 5 to about 70 with a preferred amount ranging from about 15 to about 35 parts per 100 parts of the polymer. The porosigens having a porosity of from about 0.1 to about 100 grams per 100 grams of water are generally preferred so that a quicker release of the trace nutrient is obtained.

With regard to the pesticides, the amount of porosigen is as previously set forth; that is, if the porosigen has a solubility of 0.1 or less, for example, to about 0.0005 grams per 100 grams of polymer, the amount ranges from about 15 to about 70 and from about 25 to about 60 for the organotin compound. For the other pesticides, the range is from about 5 parts to about 70 parts by weight and desirably from about 15 to about 35 parts per 100 parts of polymer. If a porosigen having a solubility of 0.1 or greater is utilized, the amount of porosigen ranges from about 1 part to about 60 parts, with 2 parts to about 20 parts being desired.

The composition, in addition to the above mentioned compounds, can contain conventional additives to enhance dispersion, add color, aid in processing, or to alter density. Thus, from about 0.2 to about 10 or 20 parts by weight of an insoluble compound such as zinc stearate per 100 parts by weight of the polymer may be utilized as a dispersant. usually, an amount up to about 5 or 10 parts, and even up to 1 or 2 parts is often used. The ability of the pesticide, including nematicides, plant regulants, etc., or trace nutrient to leave the dispensing unit and pass into the ambient environment wherein dwells the target organism is dependent upon contact with moisture. Said moisture can penetrate said dispenser via movement through a pore structure into said dispenser wherein said pesticide or trace nutrient may be solvated by ingressing moisture and thus move outward through diffusion. Such a system is termed leaching. In order to create said porosity and thus allow leaching to occur, the porosigen additive must first be solvated and removed as described above. However, in some cases, the pesticide molecule or the trace nutrient molecule may be of too great a physical size to move conveniently from the occupied spaces, or intermolecular voids, between matrix molecules. This volume, termed herein as "free volume," can at times play a critical role in release of the incorporated agent into the growing pore network. It has been discovered that free volume can be altered through the specific incorporation of a secondary polymer. Where agent molecule dimensions are large, an increase in free volume improves the rate of agent movement from the interstitial spaces into the water-filled pore. In order to increase free volume and thus improve efficacy, a secondary polymer at melt index, widely variable from the binding, or matrix, polymer is utilized. For example, if the matrix polymer has a melt index of 1.5, the secondary polymer selected would have a melt index of 6.0 or greater, a disparity of 5 to 25 melt index units being desirable.

According to the concepts of the present invention, the slow release of a compound such as the trace nutrient, the plant regulants, the various pesticide compounds which kill mosquito larva, molluscans, and other aquatic pests, the nematicides and the grub or soil insects, are slowly released from the thermoplastic or thermoset dispenser over a period of time. The mechanism of release depends upon exposure of the porosigen to moisture or water, that is with the dispenser actually residing within a body of water or residing on or in the soil and therefor subject to soil moisture. When contained in the soil, the dispenser is in integral contact therewith, and the compound is released directly into the soil. Since the porosigen is thoroughly mixed, blended, or dispensed throughout the dispenser along with the compound, various portions of the surface of the granule, pellet, etc., that is the dispenser, will contain portions of porosigen. Thus, upon contact with moisture or water, the porosigen will slowly dissolve and, through a dissolution process, creates a porous network or structure through the thermoset or thermoplastic dispenser. This permits the water to contact the thereby exposed incorporated compound, for example, trace nutrient, plant regulant, pesticide, whereby it is actually released; that is, actually drawn out of or removed from the dispenser. This solvation process of the porosigen results in the gradual and controlled release of the compound in the water over a period of time such as from a period of weeks, months, or even years.

The compound to be released, be it a plant regulant, a nematicide, a soil insecticide, etc., are insoluble in the plant matrix, but usually slightly soluble in water. Since they are thoroughly mixed or dispersed throughout the dispenser with the polymer matrix, they will not be released in any significant amounts with regard to efficacy, since water cannot penetrate to reach the agent save through the pore network, if they are released at all. However, the dispersement or mixture of the porosigen in the polymer matrix provides a pore structure and thus a suitable slow release mechanism. Moreover, should a particular compound be water soluble and/or a liquid, it is still generally slowly released in a controlled manner, since it is dispersed throughout the matrix and generally is not mobile except through the pore structure created by the porosigen.

The slow or controlled release dispenser is prepared by mixing, blending, etc., the compound, such as the trace nutrient, the pesticide, the plant regulant, the nematicide, the soil insecticide, with the thermoplastic and the porosigen in suitable proportions as indicated herein in any conventional mixing apparatus along with various additives such as colorants, dispersants, and the like. The mixture is coalesced by generally heating it above the softening point and preferably above the melting point of the thermoplastic. The result is a slow release dispenser having a polymer matrix, wherein the pesticide, trace nutrient, etc., is thoroughly mixed or dispersed, for example monolithically dispersed; that is, the compound usually exists as an individual entity or site, throughout the dispenser. Naturally, the porosigen is also mixed or dispersed throughout the dispenser. The dispenser may be made into any manner, shape, or form. Thus, if the compounds are mixed and extruded from an extruder, they may be in the form of ribbons, or chopped into pellets, chips, or the like. Naturally, the temperature of the coalescing apparatus relates to the softening or melting point of the thermoplastic and may range from about 170° C. to about 190° C., or from about 120° C. to about 220° C., although lower or higher temperatures may be utilized depending upon the thermoplastic. Additionally, the dispenser can be prepared by melt casting, solution casting, and the like, such techniques known to the plastic processing art.

Similarly, when a thermoset plastic is utilized, the pesticide, trace nutrient, etc., and the porosigen is mixed, blended, etc., at a temperature below the polymerizating temperature of the thermoset. Then, the mixture, wherein the compound is thoroughly mixed or dispersed, for example, monolithically, is heated as in an extruded or other conventional apparatus to produce the dispenser in any suitable size, shape, etc. Should the size not be suitable, etc., the matrix can be cut, chopped, etc., by conventional apparatus to achieve a suitable size, etc.

In a similar manner to the compounds set forth above, other compounds can be incorporated within the plastic dispenser utilizing generally the same techniques, process, incorporation, concepts, and the like, with or without minor modifications well known to those skilled in the art. Such compounds include plant regulants and pesticides, such as nematicides, and soil insecticides. Thus, a compound such as a plant regulant, that is a compound specifically formulated to make a specific portion of the plant grow faster than others, a nematicide, that is a compound for killing nematicides, and soil insecticides, that is a compound for killing insects that live in their larva stage in the soil, can be incorporated in the same polymers, either thermoplastic or thermosetting, generally utilizing the same teachings as set forth above, the same porosigens, and the same preparation techniques. Thus, the plant regulant, nematicide, soil insecticide, may be mixed with the porosigen and the polymer in any conventional mixing apparatus such as an extruder, a banbury mixer, etc., along with various additives such as colorants, and the like, and coalesced and formed into any particular desirable shape or size as a pellet, chip, ribbon, etc., as described above. As should be apparent from all of my prior copending specifications, so long as the porosigen and the compound are incorporated into the polymer matrix with a polymer being coalesced throughout the mixture, a porous type network will be formed and the compound will be released upon contact with water.

Generally, any plant regulant can be incorporated within the dispenser or matrix including maleic hydrazide; ethrel, (2-chloroethyl)phosphonic acid; Alor; Polaris; and Triacontanol, $CH_2(CH_2)_{29}OH$, and the like.

Generally, any nematicide can be used with specific examples including, Dasanit, that is O,O-diethyl O-[4-(methylsulfonyl)phenyl] phosphorothioate; Dichlofenthion, that is, O,O-diethyl-O-2,4-dichlorophenyl phosphorothioate; Bromophos, that is, O,O-dimethyl 0,2,5-dichloro-4-bromophenyl-phosphorothioate; Ethoprop, that is, O-ethyl S,S-dipropyl phosphorodithioate, and the like.

Generally, any ground or soil insecticide may be used. By a soil insect, it is meant any insect which has a larva or burrowing stage of life in the soil, for example, Japanese beetles. It is in this ground stage, that is, actually while within the soil, that the insect is destroyed. Specific examples of soil insecticides include Aldrin, that is, hexachlorohexahydro-endo-exodimethane naphthalene; Dieldrin, that is, hexachloroepoxy-octahydro-endo-exo-dimethanonaphthalene; Chlorodane, that is, octachloro-4,7-methanotetrahydro-indane; Temik (Aldicarb), that is, 2-methyl-2-(methylthio) propionaldehyde-O-(methylcarbamoyl) oxime; Carbofuran, that is, 2,3-dihydro-2,2-dimethyl-7-benzofuran methyl carbamate; Landrin, that is, trimethyl phenyl methylcarbamate; Chlorfenvinphos, that is, 2-chloro-1-(2,4-dichlorophenyl)vinyl diethyl phosphate; Phorate, that is, O,O-diethyl-S-[(ethylthio)methyl] phosphorodithioate; Terbufos, that is, S-test-butylthiomethyl-O-O-diethyl phosphorodithioate, and the like.

The plant regulants, dispensers of the present invention are utilized by applying them to soil, that is, on top of soil, and desirably by applying them within the soil. Although the nematicides and the soil insecticides can be applied on the soil, since the compound is effective with regard to the stage of life within the soil, it is highly preferred that these compounds contained in the dispenser be added so that they are contained within the soil. The method or manner of addition to the soil is by any conventional means such as by plowing, tilling, banding, cultivating, furrowing, and the like. Thus, the release mechanism occurs from moisture (water) in the soil. The overall amount of porosigen ranges from about 5 to about 80 parts by weight per 100 parts of polymer. Since the amount of moisture in the soil is not that existing in an aquatic environment, the high solubility porosigens are desired in the dispenser, that is, the porosigens as noted above having a solubility of from about 0.1 up to about 100 grams per 100 grams of water are preferred. The amount of high solubility porosigen ranges from about 1 to about 40 parts by weight per 100 parts of polymer in the dispenser, that is, pellet or the like, with from about 1 to about 30 parts being desired, and 12 to about 25 being preferred. When the low solubility porosigen is utilized, naturally a higher amount of porosigen is desired in order to obtain proper release rates. Generally, the amount of the low solubility porosigen, that is, a porosigen having a solubility of less than 0.1 or 0.01 ranges from about 5 to about 70 or 80 parts per 100 parts of polymer, with from about 15 to about 35 parts being preferred. The type and amount of porosigen is the same as that set forth above. That is, the porosigen should be inert with regard to the thermoplastic or thermoset plastic as well as with regard to the plant regulant, etc. Moreover, it should not be harmful to the environment, that is, the soil and the like.

The amount of plant regulant, nematicide, or ground insecticide which is incorporated into the plastic matrix or dispenser ranges from about 10 to about 160 parts per 100 parts of polymer, desirably from about 15 to about 100, and preferably from about 20 to about 50 parts by weight per 100 parts of polymer. Moreover, as previously noted, from about 1 to about 25 parts of a hygroscopic agent can be utilized to help absorb moisture.

Different trace nutrients and pesticides will release at different rates, dependent upon water solubility, partition coefficient, cohesive energy density, molecular size, and other physical and chemical properties of the agent molecule and the matrix. Moreover, different amounts of the compound can be varied as well as the amount of porosigen to give a desirable release rate, such that the items, e.g., a pest or a soil insect, is generally controlled; that is, eliminated, killed, kept in check, or the like.

POROSIGEN MODIFYING AGENTS

In addition to the porosigens of the present invention, the controlled release composition may contain porosity modifying constituents. These constituents may be combined with the porosigens to provide a multi-stage creation of the pore structure, hydroscopic attraction, inducement of porosity or other complementary features. For example, inert liquids compatible with the dispersible in the polymer such as lower aliphatic and glycols may be utilized. The glycols, which are highly water soluble, often will activate the porosigen by permitting more rapid water ingress and thus faster contact between a porosigen, such as $CaCO_3$ or $(NH_4)_2SO_4$ and water.

Another porosity constituent is soy oil, or other organic compounds similar in properties. Soy oil tends to be water insoluble and thus blocks or inhibits pore formation. Soy oil is preferred, and this constituent may be added in an amount from about 2 to about 25 and desirably from about 2 parts to about 6 parts by weight per 100 parts of polymer.

Another porosity constituent is silicon dioxide. This constituent, which is low water solubility, can be used to inhibit or slow down the growth of a pore network arising from the loss of a porosigen by water contact and solvation. This constituent may be added in an amount from about 2 parts to about 25 parts by weight per 100 parts of polymer. These other porosity constituents are not necessary for the creation of the controlled release compositions but they may be added to complement the functions of the porosigens.

EXAMPLE I

Trace Nutrients

To further illustrate the scope of the invention, zinc sulfate releasing dispensers were prepared in accordance with the recipes provided in Table I. Said recipes were mixed, extruded at 250° F. to 350° F., cooled, and pelletized or solvent cast and pelletized at room temperature. Pellets of each recipe were then immersed in demineralized water and zinc ion release periodically noted. Analyses were performed by removing an aliquot of water and determining the zinc content in accordance with the Zincon method as detailed in WATER ANALYSIS, Hach Chemical Co., Ames, Iowa, page 2-149, 1975.

Note that compounds prepared had incorporated therein either no porosigen or a "fast" porosigen—ammonium sulfate, solubility 70.6 g/100 g water at 20° C.; or a "slow" porosigen, calcium carbonate, solubility 0.0015 g/100 g water at 25° C.

Table II thus indicates the respective loss of zinc ion from compounds.

TABLE I

Controlled Release Zinc Recipes

| COMPOUND CODE | INGREDIENT (Weight by Percent) | | | | | | | | |
|---|---|---|---|---|---|---|---|---|---|
| | LDPE[1] | HDPE[2] | EVA[3] | PP[4] | PES[5] | ZST[6] | CaCO$_3$ | (NH$_3$)SO$_4$ | ZnSO$_4$ |
| 1A | 64 | — | — | — | — | 1 | 15 | — | 20 |
| 1B | 64 | — | — | — | — | 1 | — | 15 | 20 |
| 1C | 79 | — | — | — | — | 1 | — | — | 20 |
| 2A | — | 64 | — | — | — | 1 | 15 | — | 20 |
| 2B | — | 64 | — | — | — | 1 | — | 15 | 20 |
| 2C | — | 79 | — | — | — | 1 | — | — | 20 |
| 3A | — | — | 64 | — | — | 1 | 15 | — | 20 |
| 3B | — | — | 64 | — | — | 1 | — | 15 | 20 |
| 3C | — | — | 79 | — | — | 1 | — | — | 20 |
| 4A | — | — | — | 64 | — | 1 | 15 | — | 20 |
| 4B | — | — | — | 64 | — | 1 | — | 15 | 20 |
| 4C | — | — | — | 79 | — | 1 | — | — | 20 |
| 5A | — | — | — | — | 64 | 1 | 15 | — | 20 |
| 5B | — | — | — | — | 64 | 1 | — | 15 | 20 |
| 5C | — | — | — | — | 79 | 1 | — | — | 20 |

| | PAM[7] | PS[8] | EP[9] | ZST | CaCO$_3$ | (NH$_4$)$_2$SO$_4$ | ZnSO$_4$ |
|---|---|---|---|---|---|---|---|
| 6A | 65 | — | — | — | 15 | — | 20 |
| 6B | 65 | — | — | — | — | 15 | 20 |
| 6C | 80 | — | — | — | — | — | 20 |
| 7A | — | 64 | — | 1 | 15 | — | 20 |
| 7B | — | 64 | — | 1 | — | 15 | 20 |
| 7C | — | 79 | — | 1 | — | — | 20 |
| 8A | — | — | 65 | — | 15 | — | 20 |
| 8B | — | — | 65 | — | — | 15 | 20 |
| 8C | — | — | 80 | — | — | — | 20 |

[1]Low density polyethylene, Complex 1023B, Complex Co., Rolling Meadows, Illinois Extruded at 350° F.
[2]High density polyethylene, Chemplex 6001, Chemplex Co. Extruded at 350° F.
[3]Ethylene vinyl acetate copolymer, Complex 3315, Chemplex Co. (28% VA copolymer) Extruded at 250° F.
[4]Polypropylene, P-460) Honatech Inc., Yonkers, N.Y.; Extruded at 300° F.
[5]Polyester, Hytrel, E. I. DuPont Chemical Co., Wilmington, Delaware. Extruded at 350°–400° F.
[6]Zinc Stearate (dispersant)
[7]Polyamide, Elvamide 8061, E. I. DuPont de Nemours and Co., Wilmington, Delaware. Solution cast in ethyl alcohol.
[8]Polystyrene, P-400; Honatech Inc., Yonkers, N.Y.; Extruded at 400° F.
[9]Epoxy, polyester-styrene based, Dynatron Bondo Corp., Atlanta, Georgia. Heat, self-generated.

TABLE II

Release Rate Zinc Sulfate in Demineralized Water

| COMPOUND CODE | POROSIGEN | PERCENT RELEASED/DAY IMMERSED | | REMARKS |
|---|---|---|---|---|
| | | 30-day period[1] | 70-day period[2] | |
| 1A | slow | 0.31% | 0.31% | — |
| 1B | fast | 1.66% | — | Release complete in 60 days |
| 1C | none | 0.12% | 0.05% | No release after 31 days |
| 2A | slow | 0.32% | 0.20% | — |
| 2B | fast | 0.55% | — | |
| 2C | none | 0.05% | 0.02% | No release after 8 days |
| 3A | slow | 0.35% | 0.15% | — |
| 3B | fast | 1.37% | — | Release complete in 72 hours |
| 3C | none | 0.05% | 0.02% | No release after 7 days |
| 4A | slow | 0.35% | 0.19% | — |
| 4B | fast | 0.80% | — | Release complete in 40 days |
| 4C | none | 0.29% | 0.14% | — |
| 5A | slow | 0.35% | 0.16% | — |
| 5B | fast | 0.39% | 0.35% | — |
| 5C | none | 0.09% | 0.07% | — |
| 6A | slow | 0.63% | — | — |
| 6B | fast | 2.49% | — | — |
| 6C | none | 1.00% | — | — |
| 7A | slow | 0.39% | 0.23% | — |
| 7B | fast | 1.02% | 0.47% | — |
| 7C | none | 0.08% | 0.06% | — |
| 8A | slow | 5.5% | — | — |
| 8B | fast | 1.3% | — | — |
| 8C | none | 5.1% | — | — |

[1]The period covered is from immersion day 2, through immersion day 31. The initial 24-hour release is discounted in that agent on the pellet surface and not monolithically incorporated is rapidly solvated and lost.
[2]The period covered is from immersion day 2 through immersion day 71.
*Period of release was 7 days.

To further illustrate the invention, consider compounds 3A, 3B, and 3C. Table III provides greater detail as to loss in water.

TABLE III

Zinc Sulfate Loss From Ethylene Vinyl Acetate Copolymer

| COMPOUND | POROSIGEN | ACCUMULATED PERCENT LOSS OF ZINC ION | | | | |
|---|---|---|---|---|---|---|
| | | 24 hrs. | 7 days | 31 days | 40 days | 71 days |
| 3A | slow | 7.25% | 11.3% | 12.5% | 12.5% | 12.7% |
| 3B | fast | 38.25% | 88.95% | 100% | — | — |
| 3C | none | 3.25% | 4.85% | 4.85% | 4.85% | 4.85% |

Obviously, 3C, lacking porosigen, stopped emitting zinc after surface washing was completed.

Further illustration of the phenomenon is seen with elastomeric materials. Table IV provides the recipes for compounds RA, RB and RC based on natural rubber. Table V depicts loss rates.

TABLE IV

| COMPOUND CODE | R Recipes INGREDIENT (by parts) | | | |
|---|---|---|---|---|
| | Natural Rubber[1] Compound | $CaCO_3$ | $(NH_4)_2SO_4$ | ZINC SULFATE |
| RA | 100 | 15 | — | 15 |
| RB | 100 | — | 15 | 15 |
| RC | 100 | — | — | 15 |

TABLE V

Zinc Loss From Natural Rubber Compounds

| COMPOUND | POROSIGEN | % ACCUMULATED LOSS | | | |
|---|---|---|---|---|---|
| | | 1 day | 7 days | 31 days | 71 days |
| RA | fast | 4.4% | 5.4% | 5.7% | 5.7% |
| RB | slow | 0.0% | 0.3% | 0.3% | 0.3% |
| RC | none | 0.0% | 0.0% | 0.0% | 0.0% |

As can be akewed, zinc sulfate is not released from an elastomer, and even with the use of a highly soluble porosigen, only a slight amount is released, all within a few days.

NOTE: The natural rubber compound master recipe is:

| | | | |
|---|---|---|---|
| Natural Rubber | 100 parts | Stearic acid | 0.2 parts |
| Carbon black | 10 parts | Alfax | 2.0 parts |
| ZnO | 2 parts | Sulfur | 2.5 parts |
| Phenyl-β-naphthylamine | 1 part | | |

EXAMPLE II

Tributyltin Fluoride (TBTF) Recipes

TABLE VI

| COMPOUND CODE | Ingredients (Weight Percent) | | | | | | | |
|---|---|---|---|---|---|---|---|---|
| | LDPE | HDPE | EVA | $CaCO_3$ | $(NH_4)_2SO_4$ | ZnSt | TBTF | PS |
| 1A | 64 | — | — | 15 | — | 1 | 20 | — |
| 1B | 64 | — | — | — | 15 | 1 | 20 | — |
| 1C | 79 | — | — | — | — | 1 | 20 | — |
| 2A | — | 64 | — | 15 | — | 1 | 20 | — |
| 2B | — | 64 | — | — | 15 | 1 | 20 | — |
| 2C | — | 79 | — | — | — | 1 | 20 | — |
| 3A | — | — | 64 | 15 | — | 1 | 20 | — |
| 3B | — | — | 64 | — | 15 | 1 | 20 | — |
| 3C | — | — | 79 | — | — | 1 | 20 | — |
| 4A | — | — | — | 15 | — | 1 | 20 | 64 |
| 4B | — | — | — | — | 15 | 1 | 20 | 64 |
| 4C | — | — | — | — | — | 1 | 20 | 79 |

The compounds were made identical to those set forth in Example I, except that 20 parts of tributyltin fluoride (TBTF) was used instead of 20 parts of $ZnSO_4$.

Where tested against *B. Glabrata* snails, the following results were observed.

TABLE VII

Controlled Release TBTF Bioassayed Against *B. Glabrata* Snails
(30 day bioassay - 0.66 ppm - ta[1])

| COMPOUND CODE | POROSIGEN | MORTALITY TIME IN DAYS | | |
|---|---|---|---|---|
| | | $LT_{50}$ | $LT_{90}$ | $LT_{100}$ |
| 1B | Fast | 13 | 23 | 27 |
| 1C | None | 16 | 30+ | — |
| 2B | Fast | 10 | 11 | 12 |
| 2C | None | 16 | 25 | 30+ |
| 3A | Slow | 15 | 22 | 28 |
| 3B | Fast | 8 | 10 | 11 |
| 3C | None | 30+ | — | — |
| 4A | Slow | 15 | 18 | 23 |
| 4B | Fast | 7 | 9 | 10 |
| 4C | None | — | 30+ | — |

[1]The dosage used was 0.66 ppm total active agent, i.e., if all the agent were released at once, it would be the TBTF concentration in the water. In reality, life is over 2 years for each material - the water concentration would never exceed about 0.001 ppm/day.

NOTE
LT = lethal time
$LT_{50}$ = time (days) to 50% snail mortality
$LT_{90}$ = time (days) to 90% snail mortality
$LT_{100}$ = time (days) to 100% snail mortality Each bioassay was repicated 3 times with 10 healthy adult snails per replicate. Aquarias contained 100 ml of conditioned water.

EXAMPLE III

Insecticide Release

Various insecticidal agents were incorporated in a number of polymeric matrices in a manner described in Example I and evaluated against mosquito larva. Examples are provided for Temephos, Naled (dibrom), Sevin and Fenitrothion.

Bioassays were performed against *Culex pipiens* larva, at 1 ppm total active agent dosage (i.e., 1 ppm is the total amount of agent in the plastic dispensing pellet, and *not* the water concentration). Pellets were prewashed 24 hours prior to testing to remove some of the surface accumulation of the agent.

TABLE VIII

Insecticide Recipes
INGREDIENT BY WEIGHT PERCENT

| COMPOUND CODE | LDPE | HDPE | EVA | TEMEPHOS | FENITROTHION | NALED | $CaCO_3$ | $(NH_4)_2SO_4$ | ZST | PP | PES | PAM | PVAC[1] | PS | U[2] |
|---|---|---|---|---|---|---|---|---|---|---|---|---|---|---|---|
| 11A | — | 74 | — | 10 | — | — | 15 | — | 1 | — | — | — | — | — | — |
| 11B | — | 74 | — | 10 | — | — | — | 15 | 1 | — | — | — | — | — | — |
| 11C | — | 89 | — | 10 | — | — | — | — | 1 | — | — | — | — | — | — |
| 12A | — | — | 74 | 10 | — | — | 15 | — | 1 | — | — | — | — | — | — |
| 12B | — | — | 74 | 10 | — | — | — | 15 | 1 | — | — | — | — | — | — |
| 12C | — | — | 89 | 10 | — | — | — | — | 1 | — | — | — | — | — | — |
| 13A | — | — | — | 10 | — | — | 15 | — | 1 | — | 74 | — | — | — | — |
| 13B | — | — | — | 10 | — | — | — | 15 | 1 | — | 74 | — | — | — | — |

TABLE VIII-continued

Insecticide Recipes
INGREDIENT BY WEIGHT PERCENT

| COMPOUND CODE | LDPE | HDPE | EVA | TEMEPHOS | FENITROTHION | NALED | CaCO₃ | (NH₄)₂SO₄ | ZST | PP | PES | PAM | PVAC[1] | PS | U[2] |
|---|---|---|---|---|---|---|---|---|---|---|---|---|---|---|---|
| 13C | — | — | — | 10 | — | — | — | — | 1 | — | 89 | — | — | — | — |
| 14A | — | — | — | 10 | — | — | 15 | — | — | — | — | — | 75 | — | — |
| 14B | — | — | — | 10 | — | — | — | 15 | — | — | — | — | 75 | — | — |
| 14C | — | — | — | 10 | — | — | — | — | — | — | — | — | 90 | — | — |
| 15A | — | — | — | 10 | — | — | 15 | — | 1 | — | — | — | — | 74 | — |
| 15B | — | — | — | 10 | — | — | — | 15 | 1 | — | — | — | — | 74 | — |
| 15C | — | — | — | 10 | — | — | — | — | 1 | — | — | — | — | 90 | — |
| 16A | — | — | — | 10 | — | — | 15 | — | — | — | — | — | — | — | 75 |
| 16B | — | — | — | 10 | — | — | — | 15 | — | — | — | — | — | — | 75 |
| 16C | — | — | — | 10 | — | — | — | — | — | — | — | — | — | — | 90 |
| 17A | — | — | — | — | 10 | — | 15 | — | 1 | — | — | — | — | 75 | — |
| 17B | — | — | — | — | 10 | — | — | 15 | 1 | — | — | — | — | 75 | — |
| 17C | — | — | — | — | 10 | — | — | — | 1 | — | — | — | — | 90 | — |
| 18A | 74 | — | — | — | — | 10 | 15 | — | 1 | — | — | — | — | — | — |
| 18B | 74 | — | — | — | — | 10 | — | 15 | 1 | — | — | — | — | — | — |
| 18C | 89 | — | — | — | — | 10 | — | — | 1 | — | — | — | — | — | — |
| 19A | — | 74 | — | — | — | 10 | 15 | — | 1 | — | — | — | — | — | — |
| 19B | — | 74 | — | — | — | 10 | — | 15 | 1 | — | — | — | — | — | — |
| 19C | — | 89 | — | — | — | 10 | — | — | 1 | — | — | — | — | — | — |
| 20A | — | — | — | — | — | 10 | 15 | — | 1 | 74 | — | — | — | — | — |
| 20B | — | — | — | — | — | 10 | — | 15 | 1 | 74 | — | — | — | — | — |
| 20C | — | — | — | — | — | 10 | — | — | 1 | 89 | — | — | — | — | — |
| 21A | — | — | — | — | — | 10 | 15 | — | — | — | — | 75 | — | — | — |
| 21B | — | — | — | — | — | 10 | — | 15 | — | — | — | 75 | — | — | — |
| 21C | — | — | — | — | — | 10 | — | — | — | — | — | 90 | — | — | — |
| 22A | — | — | — | — | — | 10 | 15 | — | 1 | — | — | — | — | 74 | — |
| 22B | — | — | — | — | — | 10 | — | 15 | 1 | — | — | — | — | 74 | — |
| 22C | — | — | — | — | — | 10 | — | — | 1 | — | — | — | — | 89 | — |

[1]Polyvinyl acetate, Ayac, Union Carbide Chemicals Co., Cleveland, Ohio. Solution cast in acetone.
[2]Polyurethane, 5701F₁, B. F. Goodrich Chemical Co., Cleveland, Ohio. Solution cast in tetrahydrofuran.

TABLE IX

Mosquito Larva Bioassay (2nd Instar C. pipiens pipiens)

| COMPOUND CODE | AGENT | POROSIGEN | PERCENT MOSQUITO MORTALITY BY DAYS | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| 11A | Temephos | slow | 7 | 37 | 73 | 73 | 86 | 100 | — | — | — | — | — | — | — | — |
| 11B | Temephos | fast | 27 | 70 | 87 | 100 | — | — | — | — | — | — | — | — | — | — |
| 11C | Temephos | none | 0 | 27 | 37 | 40 | 40 | 47 | 53 | 57 | 60 | 67 | 70 | * | — | — |
| 12A | Temephos | slow | 0 | 9 | 30 | 33 | 60 | 63 | 70 | 70 | 73 | * | — | — | — | — |
| 12B | Temephos | fast | 15 | 43 | 47 | 93 | 100 | — | — | — | — | — | — | — | — | — |
| 12C | Temephos | none | 7 | 14 | 17 | 20 | 27 | 33 | 40 | 100 | — | — | — | — | — | — |
| 13A | Temephos | slow | 0 | 7 | 13 | 30 | 43 | 53 | 67 | 73 | 100 | — | — | — | — | — |
| 13B | Temephos | fast | 21 | 63 | 77 | 83 | 100 | — | — | — | — | — | — | — | — | — |
| 13C | Temephos | none | 0 | 3 | 7 | 17 | 23 | 23 | 37 | 37 | 37 | 40 | 40 | 40 | 43 | * |
| 14A | Temephos | slow | 0 | 13 | 17 | 17 | 17 | 23 | 30 | 40 | 43 | 57 | 67 | 90 | 90 | 93 |
| 14B | Temephos | fast | 10 | 17 | 23 | 27 | 43 | 97 | 100 | — | — | — | — | — | — | — |
| 14C | Temephos | none | 0 | 0 | 3 | 13 | 13 | 13 | 17 | 27 | 33 | 47 | 57 | * | — | — |
| 15A | Temephos | slow | — | — | — | — | — | — | — | — | — | — | — | — | — | — |
| 15B | Temephos | fast | 23 | 37 | 50 | 63 | 67 | 67 | 83 | 100 | — | — | — | — | — | — |
| 15C | Temephos | none | 0 | 10 | 13 | 17 | 17 | 17 | 20 | 40 | 40 | * | — | — | — | — |
| 16A | Temephos | slow | — | — | — | — | — | — | — | — | — | — | — | — | — | — |
| 16B | Temephos | fast | 17 | 177 | 97 | 97 | 100 | — | — | — | — | — | — | — | — | — |
| 16C | Temephos | none | 10 | 13 | 13 | 13 | 17 | 27 | 30 | 30 | 33 | * | — | — | — | — |
| 17A | Fenitrothion | slow | — | — | — | — | — | — | — | — | — | — | — | — | — | — |
| 17B | Fenitrothion | fast | 47 | 50 | — | — | — | — | — | — | — | — | — | — | — | — |
| 17C | Fenitrothion | none | 0 | 3 | — | — | — | — | — | — | — | — | — | — | — | — |
| 18A | Naled | slow | 30 | 43 | 53 | 57 | 73 | 73 | * | — | — | — | — | — | — | — |
| 18B | Naled | fast | 50 | 100 | — | — | — | — | — | — | — | — | — | — | — | — |
| 18C | Naled | none | 33 | 40 | 40 | 40 | * | — | — | — | — | — | — | — | — | — |
| 19A | Naled | slow | — | — | — | — | — | — | — | — | — | — | — | — | — | — |
| 19B | Naled | fast | 30 | 33 | 33 | 43 | 53 | 67 | 77 | 83 | — | — | — | — | — | — |
| 19C | Naled | none | 17 | 20 | 20 | 33 | 40 | 40 | 40 | 43 | — | — | — | — | — | — |
| 20A | Naled | slow | — | — | — | — | — | — | — | — | — | — | — | — | — | — |
| 20B | Naled | fast | 30 | 43 | 47 | 50 | 53 | 57 | 63 | 70 | — | — | — | — | — | — |
| 20C | Naled | none | 0 | 7 | 7 | 7 | 7 | * | — | — | — | — | — | — | — | — |
| 21A | Naled | slow | 20 | 20 | 27 | 27 | 27 | * | — | — | — | — | — | — | — | — |
| 21B | Naled | fast | 10 | 13 | 30 | 37 | 43 | 70 | — | — | — | — | — | — | — | — |
| 21C | Naled | none | 0 | 13 | 13 | 27 | 30 | 30 | * | — | — | — | — | — | — | — |
| 22A | Naled | slow | — | — | — | — | — | — | — | — | — | — | — | — | — | — |
| 22B | Naled | fast | 23 | 73 | 100 | — | — | — | — | — | — | — | — | — | — | — |
| 22C | Naled | none | 10 | 10 | 20 | 23 | 30 | 33 | 33 | 33 | — | — | — | — | — | — |

TABLE IX-continued

Mosquito Larva Bioassay (2nd Instar C. *pipiens pipiens*)

| COMPOUND CODE | AGENT | POROSIGEN | \multicolumn{14}{c}{PERCENT MOSQUITO MORTALITY BY DAYS} | | | | | | | | | | | | | |
|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| Control | Naled | — | 0 | 0 | 0 | 7 | 10 | 13 | 20 | 27 | 37 | * | | | | |

* = pupation and adult emergence occurs

EXAMPLE IV

To further illustrate the long term agent release incident to the controlled release material, the formation of Table X immersed in water and said water periodically analyzed for agent concentration. Said analysis allows the computation of a release rate. Table XI illustrates this data. Since the loss rate is known (60 days) and the amount of agent incorporated in said formulation, a release life projection can be derived.

TABLE X

RECIPES

| EXAMPLE | LDPE | EVA | TEMEPHOS | ZnSt | $CaCO_3$ | $(NH_4)_2SO_4$ |
|---|---|---|---|---|---|---|
| 23A | 74 | — | 10 | 1 | 15 | — |
| 23B | 74 | — | 10 | 1 | — | 15 |
| 23C | 89 | — | 10 | 1 | — | — |

TABLE XI

Release Rate and Extrapolated Lifetime of Controlled Release Temephos

| EXAMPLE | POROSIGEN | RELEASE RATE Micrograms/ gram-liter-day | RELEASE LIFE (years) |
|---|---|---|---|
| 23A | $CaCO_3$ | 8.0 | 48.0 |
| 23B | $(NH_4)_2SO_4$ | 15.9 | 12.4 |
| 23C | none | 2.0 | ineffective |

EXAMPLE V

The ethanolamine salt of niclosamide was dispensed in several thermoplastic matrices, extruded at 190° F., pelletized and evaluated against *Biomphlaria glabrata* snails at various dosages. Table XII depicts the recipes used and Table XIII, the bioassay results. It is noted that these finely tuned recipes depend upon an increase in free volume created by the use of polymer alloys of low density polyethylene (MN718) and ethylene-propylene copolymer (Vistalon 702). The porosigen system is a mix of a low water solubility porosigenic agent and a high water solubility agent.

TABLE XII

Ethanolamine Niclosamide Recipes

| INGREDIENT | Example 26 | 27 | 28 |
|---|---|---|---|
| Vistalon 702 | 33 | 27 | 25 |
| MN 718 | 33 | 27 | 25 |
| Zinc Stearate | 1.2 | 1 | 1 |
| Niclosamide | 12.5 | 30 | 30 |
| $CaCO_3$ | 12.5 | 5 | 13 |
| $(NH_4)_2SO_4$ | 8 | 10 | 7 |

TABLE XIII

Bioassay: Controlled Release Ethanolamine Niclosamide Versus *B. glabrata* Snails (30-Day Evaluation)

| EXAMPLE | DOSAGE (total active) | $LT_{50}$ | $LT_{90}$ | $LT_{100}$ |
|---|---|---|---|---|
| 26 | 5 ppm | 15 | 24 | — |
| | 1 ppm | 16 | 28 | — |
| | 0.5 ppm | 20 | — | — |
| 27 | 5 ppm | 20 | — | — |
| | 1 ppm | 20 | — | — |
| | 0.5 ppm | 20 | — | — |
| 28 | 5 ppm | 2 | 3 | 10 |
| | 1 ppm | 20 | 22 | 25 |
| | 0.5 ppm | 20 | 22 | 25 |

NOTE: Wherein the ratio of $CaCO_3$:$(NH_4)_2SO_4$ is 5:10 resulting kill rate is very slow, however, at a $CaCO_3$:$(NH_4)_2SO_4$ ratio of 13:7, an $LT_{100}$ is achieved within 10 to 25 days depending on dosage.

EXAMPLE VI

Soil Insecticides and Nematicides

Various materials such as N,N-dimethyl dodecanamide (NNDD), a nematicide, chloropyrifos and turbophos, soil insecticides, have been prepared as controlled release materials and applied to soil. Table XIV illustrates several chloropyrifos recipes and Table XV shows release rate in soil.

TABLE XIV

Chloropipifros Recipes (In a soil inseticide recipe)

| EXAMPLE | EVA | LDPE | ZnSt | $(NH_4)_2SO_4$ | CHLOROPYRIFOS |
|---|---|---|---|---|---|
| 29 | 50 | 40 | 1 | 10 | 15 |
| 30 | 50 | 40 | 1 | 10 | 8 |
| 31 | 100 | — | 1 | 10 | 20 |
| 32 | 100 | — | 1 | 10 | 10 |

TABLE XV

| EXAMPLE | % CHLOROPIPIFOS LOSS PER WEEK |
|---|---|
| 29 | 4.5-4.8% |
| 30 | 5.7-6.1% |
| 31 | 4.9-5.1% |
| 32 | 3.8-4.0% |

While in accordance with the patent statutes, the preferred embodiments of the invention have been described in detail, for the true scope of the invention, reference should be had to the appended claims.

What is claimed is:

1. A floating controlled release pesticide dispenser, comprising:

a polymer, an aquatic pesticide, and a porosity inducing agent, said polymer in the form of a matrix and containing said aquatic pesticide and said porosity inducing agent, the amount of said polymer being 100 parts by weight, said polymer of said matrix selected from the group consisting of a thermoplastic polymer, a thermoset polymer, and combinations thereof;

said aquatic pesticide being a pesticide for destroying aquatic pests in an aqueous environment, the amount of said pesticide ranging from about 2 parts by weight to about 80 parts by weight per 100 parts of said polymer except when said pesticide is an organotin compound, the amount of said organotin compound ranging from about 25 to about 75 parts; and said aquatic pesticide slowly being released from the dispenser;

said dispenser having a density of less than 1.0 grams per cc; and an anchor, said anchor having a density of greater than 1.0 grams per cc and connected to said dispenser.

2. A floating controlled release pesticide dispenser according to claim 1, wherein said thermoplastic polymers are selected from the group consisting of polyolefins made from monomers having from 2 to 10 carbon atoms, polystyrene, substituted polystyrene, the acrylic polymers, the polyvinyl ethers, the polyvinyl acetals, the halogen-containing polymers, the nylons, the polyethers, polyesters, polyurethanes, the cellulose plastics, and combinations thereof, and wherein said thermoset polymers are selected from the group consisting of phenolics, the epoxides, the amino resins, the unsaturated polyesters, the urethane foams, the silicone polymers, and combinations thereof.

3. A floating controlled release pesticide dispenser according to claim 2, wherein the porosity of said porosity agent is 0.1 grams or less per 100 grams of water, wherein the amount of said porosity agent ranges from about 5 to about 70 parts per 100 parts of polymer except for said organotin compound in which the amount of porosity agent ranges from about 15 to about 70 parts.

4. A floating controlled release pesticide dispenser according to claim 3, wherein said pesticide is selected from the group consisting of tetramethyl-O,O'-thiodi-p-phenylene phosphorothioate; O,O-diethyl-O-(3,5,6-trichloro-2-pyridyl) phosphorothioate; O,O-dimethyl phosphorodithioate ester of diethyl mercaptosuccinate, a compound having the formula $R_3Sn_nX$ where $R_3$ is selected from the group consisting of an alkyl group having from 1 to 8 carbon atoms, an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms, or an

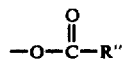

group where R" is an alkyl having from 1 to 12 carbon atoms; 2-(1-methylethoxy)phenyl methylcarbamate; dimethyl-1,2-dibromo-2,2-dichloroethyl phosphate; 6,7,8,9,10,10a-hexachloro-1,5,5a,6,9,9a-hexahydro-6,-methano-2,4,3-benzodioxathiepen-3-oxide; 1-naphthyl methylcarbamate; gamma-1,2,3,4,5,6-hexachlorocyclohexane; 2-(1-methylethoxy)phenol methylcarbamate; 1,2,12,12a-tetrahydro-2-isopropenyl-8,9-dimethyl-(1)-benzopyrano-(3,4,6)-furo-(2,3,6)(1)-benzopyran-6(6a)H-one; dichlorodiphenyltrichloroethane; 2,2-bis(p-methoxyphenyl)-1,1,1-trichloroethane; N-[(4-chlorophenyl)(amino)(carbonyl)]-2,6-difluorobenzamide; dimethyl 2,2-dichlorovinyl phosphate; O,O-dimethyl-O-(3-methyl-4-nitrophenyl) phosphorothioate; O,O-dimethyl-O-[3-methyl-4-(methylthio)phenyl] phosphorothioate; O,O-diethyl-O-O(3,5,6-trichloro-2-pyridyl)phosphorothioate; O,O-dimethyl-S-(N-methylcarbomoyl methyl)phosphorothioate; and O,O-dimethyl phosphorodithioate, S-ester with 4-(mercaptomethyl)-2-methoxy-1,3,4-thiodazoline 5-one.

5. A floating controlled release pesticide dispenser according to claim 4, wherein said porosity agent is selected from the group consisting of an oxide and a salt, said oxide and said having a cation selected from the group consisting of the alkaline metals, the alkaline earth metals, iron, zinc, nickel, silver, and tin, and said salt having an anion selected from the group consisting of a carbonate, bicarbonate, nitrate, nitrite, nitride, peroxide, phosphate, phosphite, phosphide, sulfate, sulfite, and sulfide, which have a solubility of less than 0.1 grams per 100 grams of water.

6. A floating controlled release pesticide dispenser according to claim 5, wherein said thermoplastic polymer has a number average molecular weight of from about 10,000 to about 1,000,000 and wherein said thermoset polymer is crosslinked, said polymer selected from the group consisting of polyethylene including low density polyethylene or high density polyethylene, polypropylene, a copolymer of ethylene and propylene, a copolymer of ethylene-vinyl acetate, polybutylene, polystyrene, poly-alpha-methylstyrene, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, polyvinylidene fluoride, polyamide, polyoxymethylene, polyethyleneterephthalate, cellophane, rayon, a copolymer of ethylene-propylene, and combinations thereof.

7. A floating controlled release pesticide dispenser according to claim 6, wherein the amount of said pesticide ranges from about 3 to about 50 parts, wherein the amount of said organotin compound ranges from about 40 to about 70 parts, wherein the amount of said porosity agent ranges from about 15 to about 35 parts, and wherein the amount of said porosity agent for said organotin compound ranges from about 25 to about 60 parts, and wherein said organotin compound is tributyltin oxide or tributyltin fluoride.

8. A floating controlled release pesticide dispenser according to claim 7, wherein said thermoplastic polymer is selected from the group consisting of polyethylene, a copolymer of ethylene-vinylacetate, polypropylene, polystyrene, polyester, and combinations thereof; and wherein said thermoset polymer is selected from the group consisting of epoxy, phenolic, and combinations thereof, and wherein said porosity agent has a porosity of 0.01 grams or less per 100 grams of water.

9. A floating controlled release pesticide dispenser according to claim 8, wherein said porosity-inducing agent is selected from the group consisting of magnesium carbonate, calcium carbonate, and strontium carbonate.

10. A floating controlled release pesticide dispenser according to claim 9, wherein said pesticide is selected from the group consisting of tributyltin fluoride, tributyltin oxide, O,O,O',O'-tetramethyl-O,O-thiodi-p-phenylene phosphorothioate; O,O-diethyl-O-(3,5,6-trichloro-2-pyridyl)phosphorothioate; O,O-dimethyl phosphorodithioate ester of diethyl mercaptosuccinate; dimethyl-1,2-dibromo-2,2-dichloroethyl phosphate; O,O-dimethyl-O-(3-methyl-4-nitrophenyl)phosphorothioate; and combinations thereof.

11. A floating controlled release pesticide dispenser according to claim 2, wherein said porosity agent has a solubility of from about 0.1 to about 100 grams per 100 grams of water, and wherein the amount of said porosity agent ranges from about 1 to about 60 parts by weight per 100 parts of said polymer.

12. A floating controlled release pesticide dispenser according to claim 11, wherein said pesticide is selected from the group consisting of tetramethyl-O,O'-thiodi-p-phenylene phosphorothioate; O,O-diethyl-O-(3,5,6-trichloro-2-pyridyl)phosphorothioate; O,O-dimethyl phosphorodithioate ester of diethyl mercaptosuccinate, a compound having the formula $R_3S_nX$ where $R_3$ is selected from the group consisting of an alkyl group having from 1 to 8 carbon atoms, an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms, or an

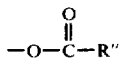

group wherein R" is an alkyl having from 1 to 12 carbon atoms; dimethyl-1,2-dibromo-2,2-dichloroethyl phosphate; 6,7,8,9,10,10a-hexachloro-1,5,5a,6,9,9a-hexahydro-6,9-methano-2,4,3-benzodioxathiepen-3-oxide; 1-naphthyl methylcarbamate; gamma-1,2,3,4,5,6-hexachlorocyclohexane; 2-(1-methylethoxy)phenol methylcarbamate; 1,2,12,12a-tetrahydro-2-isopropenyl-8,9-dimethoxy-(1)-benzopyrano-(3,4,6)-furo-(2,3,6)(1)-benzopyran-6(6a)H-one; dichlorodiphenyltrichloroethane; 2,2-bis(p-methoxyphenyl)-1,1,1-trichloroethane; N-[(4-chlorophenyl)(amino)(carbonyl)]-2,6-difluorobenzamide; dimethyl 2,2-dichlorovinyl phosphate; O,O-dimethyl,O-(3-methyl-4-nitrophenyl) phosphorothioate; O,O-dimethyl-O-[3-methyl-4-(methylthio)phenyl]phosphorothioate; O,O-diethyl-O-(3,5,6-trichloro-2-pyridyl)phosphorothioate; O,O-dimethyl-S-(N-methylcarbomoyl methyl)phosphorodithioate; and O,O-dimethyl phosphorodithioate, S-ester with 4-(mercaptomethyl)-2-methoxy-1,3,4-thiodiazoline 5-one.

13. A floating controlled release pesticide dispenser according to claim 12, wherein said thermoplastic polymer has a number average molecular weight of from about 10,000 to about 1,000,000 and said thermoplastic polymer is crosslinked, said polymer selected from the group consisting of polyethylene including low density polyethylene or high density polyethylene, a copolymer of ethylene and propylene, a copolymer of ethylene-vinylacetate, polypropylene, polybutylene, polystyrene, poly-alpha-methylstyrene, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, polyvinylidene fluoride, polyamide, polyoxymethylene, polyethyleneterephthalate, cellophane, rayon, and combinations thereof.

14. A floating controlled release pesticide dispenser according to claim 13, wherein the amount of said pesticide ranges from about 3 to about 50 parts, wherein the amount of said organotin pesticide ranges from about 40 to about 70 parts, wherein the amount of said porosity agent ranges from about 2 to about 20 parts per 100 parts of polymer, wherein said porosity agent is selected from the group consisting of halogenated metals, the halogenated alkaline earth metals, halogenated nickel, halogenated tin, halogenated silver, ammonium bromide, ammonium carbonate, ammonium chlorate, ammonium chloride, ammonium fluoride, ammonium sulfate, sodium carbonate, and sodium bicarbonate.

15. A floating controlled release pesticide dispenser according to claim 3, 4, 6, or 8, wherein said porosity agent has a solubility of from about 0.1 to about 0.0005.

16. A floating controlled release pesticide dispenser according to claim 1, 3, 4, 6, 8, 9, 10, 11, 12 or 13, wherein said anchor causes said floating dispenser to reside within an aqueous environment.

17. A floating controlled release pesticide dispenser according to claim 16, wherein said anchor weighs from about 2 to about 10 times the amount of said floating dispenser.

18. A floating controlled release pesticide dispenser according to claim 16, wherein said floating dispenser is in the form of strands.

19. A floating controlled release pesticide dispenser according to claim 16, wherein said floating dispenser is in the form of a bimodal pellet.

20. A floating controlled release pesticide dispenser according to claim 16, wherein said floating dispenser is in the form of a chip.

21. A controlled release pesticide dispenser, comprising:
a polymer, an aquatic pesticide, and a porosity inducing agent,
said polymer in the form of a matrix and containing said aquatic pesticide and said porosity inducing agent,
the amount of said polymer being 100 parts by weight, said polymer selected from the group consisting of a thermoplastic polymer, a thermoset polymer, and combinations thereof,
said aquatic pesticide being a pesticide for destorying animal aquatic pests in an aqueous environment, the amount of said pesticide ranging from about 2 parts to about 80 parts by weight per 100 parts of said polymer, except when said pesticide is an organotin compound, the amount of said organotin compound ranging from about 25 to about 75 parts, and
said aquatic pesticide slowly being released from the dispenser, and porosity agent having a solubility of 100 grams or less per 100 grams of water.

22. A controlled release pesticide dispenser according to claim 21, wherein said pesticide is selected from the group consisting of tetramethyl-O,O'-thiodi-p-phenylene phosphorothioate; O,O-diethyl-O-(3,5,6-trichloro-2-pyridyl)phosphorothioate; O,O-dimethyl phosphorodithioate ester of diethyl mercaptosuccinate, a compound having the formula $R_3S_nX$ where $R_3$ is selected from the group consisting of an alkyl group having from 1 to 8 carbon atoms, an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms; 2-(1-methylethoxy)phenol methylcarbamate, dimethyl-1,2-dibromo-2,2-dichloroethyl phosphate; 6,7,8,9,10,10a-hexachloro-1,5,5a,6,9,9a-hexahydro-6,9-methano-2,4,3-benzodioxathiepen-3-oxide; 1-naphthyl methylcarbamate; gamma-1,2,3,4,5,6-hexachlorocyclohexane; 2-(1-methylethoxy) phenol methylcarbamate; 1,2,12,12a-tetrahydro-2-isopropenyl-8,9-dimethoxy-(1)-benzopyrano-(3,4,6)-furo-(2,3,6)(1)-benzopyran-6(6a)H-one; dichlorodiphenyltrichloroethane; 2,2-bis(p-methoxyphenyl)-1,1,1-trichloroethane; N-[(4-chlorophenyl)(amino)(carbonyl]-2,6-difluorobenzamide; dimethyl 2,2-dichlorovinyl phosphate; O,O-dimethyl,O-(3-methyl-4-nitrophenyl) phosphorothioate; O,O-dimethyl-O-[3-methyl-4-methylthio)phenyl]phosphorothioate; O,O-diethyl-O-(3,5,6-trichloro-2-pyridyl)phosphorothioate; O,O-dimethyl-S-(N-methylcarbomoyl methyl)phosphorodithioate; and O,O-dimethyl phosphorodithioate, S-ester with 4-(mercaptomethyl)-2-methoxy-1,3,4-thiadiazoline 5-one.

23. A controlled release pesticide dispenser according to claim 22, wherein said porosity agent has a solubility of less than 0.1 grams per 100 grams of water, wherein the amount of said porosity agent ranges from about 5 to about 70 parts except for said organotin compound in which the amount of porosity agent ranges from about 15 to about 70 parts by weight per 100 parts of polymer.

24. A controlled release pesticide dispenser according to claim 23, wherein said thermoplastic polymers are selected from the group consisting of polyolefins made from monomers having from 2 to 10 carbon atoms, polystyrene, substituted polystyrene, the acrylic polymers, the polyvinyl ethers, the polyvinyl acetals, the halogen-containing polymers, the nylons, the polyethers, polyesters, polyurethanes, the cellulose plastics, and combinations thereof, and wherein said thermoset polymers are selected from the group consisting of phenolics, the epoxides, the amino resins, the unsaturated polyesters, the urethane foams, the silicone polymers, and combinations thereof.

25. A controlled release pesticide dispenser according to claim 24, wherein said thermoplastic polymer has a number average molecular weight of from about 10,000 to about 1,000,000 and said thermoset polymer is crosslinked, said polymer selected from the group consisting of polyethylene, low density polyethylene, high density polyethylene, a copolymer of ethylene-vinylacetate, a copolymer of ethylene and propylene, polypropylene, polybutylene, polystyrene, poly-alpha-methylstyrene, polymethylacrylate, polyacrylate, polymethylmethacrylate, polyvinyl acetate, polyvinyl butyral, polyvinyl chloride, polytetrafluoroethylene, polychlorothrifluoroethylene, polyvinyl fluoride, polyvinylidene fluoride, polyamide, polyoxymethylene, polyethyleneterephthalate, cellophane, rayon, and combinations thereof.

26. A controlled release pesticide dispenser according to claim 25, wherein the amount of said pesticide ranges from about 3 to about 50 parts, wherein the amount of said organotin compound ranges from about 40 to about 70 parts, wherein the amount of said porosity agent ranges from about 15 to about 35 parts, and wherein the amount of said porosity agent for said organotin compound ranges from about 25 to about 60 parts, and wherein said organotin compound is tributyltin oxide or tributyltin fluoride, and wherein said porosity agent has a solubility of less than 0.01 grams per 100 grams of water.

27. A controlled release pesticide dispenser according to claim 22, wherein said porosity agent has a solubility of from about 0.1 to about 100 grams per 100 grams of water, and wherein the amount of said porosity agent ranges from about 1 to about 60 parts by weight per 100 parts of said polymer.

28. A controlled release pesticide dispenser according to claim 27, wherein the amount of said pesticide ranges from about 3 to about 50 parts, wherein the amount of said organotin pesticide ranges from about 40 to about 70 parts, wherein the amount of said porosity agent ranges from about 2 to about 20 parts per 100 parts of said polymer, and wherein said polymer is selected from the group consisting of polyethylene including low density polyethylene or high density polyethylene, polypropylene, polybutene, polystyrene, poly-alpha-methylstyrene, polymethylmethalate, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, polyvinylidene fluoride, polyamide, polyoxymethylene, polyethyleneterephthalate, cellophane, rayon, and combinations thereof.

29. A controlled release pesticide dispenser according to claim 28, wherein said thermoplastic polymer has a number average molecular weight of from about 10,000 to about 1,000,000 and said thermoset polymer is crosslinked, said porosity agent is selected from the group consisting of halogenated metals, the halogenated alkaline earth metals, halogenated nickel, halogenated tin, halogenated silver, ammonium bromide, ammonium carbonate, ammonium chlorate, ammonium chloridem ammonium fluoride, ammonium sulfate, sodium carbonate, and sodium bicarbonate.

30. A process for preparing a controlled release pesticide dispenser, comprising the steps of:
adding and mixing 100 parts by weight of a polymer, from about 2 to about 80 parts by weight per 100 parts of polymer of an aquatic pesticide except when said aquatic pesticide is an organotin compound, the amount of said organotin compound ranging from about 25 to about 75 parts, and a porosity inducing agent, said polymer selected from the group consisting of a thermoplastic polymer, a thermoset polymer, and combinations thereof;
forming a floating polymer matrix dispenser, said dispenser having a density of less than 1.0 grams per cc,
attaching said dispenser to an anchor, said anchor having a density of greater than 1.0 grams per cc.

31. A process according to claim 30, wherein said polymer is selected from the group consisting of polyethylene, a copolymer of ethylene-vinylacetate, a copolymer of ethylene and propylene, polypropylene, polystyrene, a polyester and combinations thereof, or in said thermoset polymer which is selected from the group consisting of an epoxy, a phenolic, and combinations thereof, wherein said porosity agent is a compound having a solubility of less than 0.01 grams per 100 grams of water, the amount of said porosity agent ranging from about 5 to about 70 parts per 100 parts of polymer, except for said organotin compound in which said porosity agent ranges from about 15 to about 70 parts.

32. A method for preparing a slow release pesticide dispenser, comprising the steps of:

adding and mixing 100 parts by weight of a polymer, an aquatic pesticide for use in an aqueous environment for destroying aquatic pests, and a porosity inducing agent having a solubility of 100 grams or less per 100 grams of water, the amount of said pesticide ranging from about 2 parts to about 80 parts by weight per 100 parts of said polymer, except wherein said pesticide is an organotin compound, the amount of said organotin compound ranging from about 25 parts to about 75 parts by weight per 100 parts of said polymer; and forming a polymer matrix dispenser so that upon contact with an aqueous environment, said pesticide is slowly released therefrom.

said polymer selected from the class consisting of a thermoplastic and a thermoset.

33. A method for the controlled release of pesticides from a floating dispenser into an aquatic environment, comprising:

(a) dispersing a floating matrix into the environment, said matrix comprising a polymer, an aquatic pesticide for destroying aquatic pests, and a porosity inducing agent, said polymer selected from the group consisting of a thermoplastic polymer and a thermoset polymer;

(b) dissolving said porosity agent from said matrix at a controlled rate upon contact with water, to create a pore structure in said matrix;

(c) dislodging said aquatic pesticide through said pore structure from said matrix upon contact with water, said pesticide to retard or destroy undesired pests;

said porosity agent having a water solubility less than 100 grams per 100 grams of water and said polymer being water insoluble and non-porous;

said dispenser having a density of less than 1.0 grams per cc; and an anchor, said anchor having a density of greater than 1.0 grams per cc and connected to said dispenser.

34. A method for the controlled release of pesticides into an environment, according to claim 33, wherein said matrix further comprises a porosity agent modifying compound.

35. A composition for destroying aquatic pests, comprising:

a mixture of an aquatic pesticidally effective active ingredient which is water dispersible and an inert particulate material having a water solubility from less than 100 grams per 100 grams of water at 25° C.;

said mixture being dispersed within a water insoluble, non-porous polymer matrix, and being floatable;

said polymer selected from the group consisting of a thermoplastic and a thermoset, the proportion of particulate material being sufficient to induce liquid porosity in said matrix upon exposure to water; and an anchor, said anchor connected to said floatable mixture.

36. A method for the controlled release of pesticides in an environment, comprising:

(a) dispersing a matrix into the environment, said matrix comprising an aquatic pesticide for destroying pests, and a porosity inducing agent, said polymer selected from the group consisting of a thermoplastic and a thermoset;

(b) dissolving said porosity agent from said matrix at a controlled rate upon contact with water, to create a pore structure in said matrix;

(c) dislodging said aquatic pesticide through said pore structure from said matrix upon contact with water, said pesticide to retard or destroy undesired pests; and said porosity agent having a water solubility less than 100 grams per 100 grams of water and said polymer being water insoluble and non-porous.

37. A method for the controlled release of pesticides into an environment, according to claim 36, wherein said matrix further comprises a porosity agent modifying compound.

38. A composition for destroying aquatic pests, comprising:

a mixture of an aquatic pesticidally effective active ingredient which is water dispersible and an inert particulate material having a water solubility from less than 100 grams per 100 grams of water at 25° C.;

said mixture being dispersed within a water insoluble, non-porous polymer matrix, said polymer selected from the group consisting of a thermoplastic, and a thermoset;

the proportion of particulate material being sufficient to induce liquid porosity in said matrix upon exposure to water.

39. A floating controlled release pesticide dispenser according to claim 1, further comprising a second of said polymer selected from the group consisting of said thermoplastic and said thermoset, said second polymer having a melt index, said second polymer index having a disparity from said first polymer melt index of from about 5 to about 25 melt index units so that a free volume within said dispenser is created.

40. A floating controlled release pesticide dispenser according to claim 1, wherein said porosity agent creates a pore structure in said matrix upon exposure to water.

41. A floating controlled release pesticide dispenser according to claim 1, wherein said matrix further comprises a porosity agent modifying compound.

42. A process according to claim 30, further comprising adding a second of said polymer selected from the group consisting of said thermoplastic and said thermoset, said second polymer having a melt index, said second polymer index having a disparity from said first polymer melt index of from about 5 to about 25 melt index units so that a free volume within said dispenser is created.

43. A process according to claim 30, creating a pore structure with said porosity agent in said matrix upon exposure to water.

44. A process according to claim 30, further comprising adding a porosity agent modifying compound.

45. A controlled release pesticide dispenser according to claim 21, further comprising a second of said polymer selected from the group consisting of said thermoplastic and said thermoset, said second polymer having a melt index, said second polymer index having a disparity from said first polymer melt index of from about 5 to about 25 melt index units so that a free volume within said dispenser is created.

46. A controlled release pesticide dispenser according to claim 21, wherein said porosity agent creates a pore structure in said matrix upon exposure to water.

47. A controlled release pesticide dispenser according to claim 21, wherein said matrix further comprises a porosity agent modifying compound.

48. A process according to claim 32, further comprising adding a second of said polymer selected from the group consisting of said thermoplastic and said thermoset, said second polymer having a melt index, said second polymer index having a disparity from said first polymer melt index of from about 5 to about 25 melt index units so that a free volume within said dispenser is created.

49. A process according to claim 32, creating a pore structure with said porosity agent in said matrix upon exposure to water.

50. A process according to claim 32, further comprising adding a porosity agent modifying compound.

51. A controlled release pesticide dispenser according to claim 26, wherein said porosity agent is selected from the group consisting of magnesium carbonate, calcium carbonate, and strontium carbonate,
wherein said thermoplastic polymer is selected from the group consisting of polyethylene, a copolymer of ethylene-vinylacetate, polypropylene, polystyrene, polyester, and combinations thereof; and
wherein said thermoset polymer is selected from the group consisting of epoxy, phenolic, and combinations thereof.

* * * * *